United States Patent
Zhang et al.

(10) Patent No.: US 7,615,008 B2
(45) Date of Patent: *Nov. 10, 2009

(54) PROCESSING AND DISPLAYING BREAST ULTRASOUND INFORMATION

(75) Inventors: Wei Zhang, Union City, CA (US); Shih-Ping Wang, Los Altos, CA (US); Jiayu Chen, Palo Alto, CA (US); Zengpin Yu, Palo Alto, CA (US); Tommy Earl Cupples, Columbia, SC (US); Thomas P. Neff, Newark, CA (US); Michael E. Reed, Sunnyvale, CA (US)

(73) Assignee: U-Systems, Inc., San Jose, CA (US)

( * ) Notice: Subject to any disclaimer, the term of this patent is extended or adjusted under 35 U.S.C. 154(b) by 634 days.

This patent is subject to a terminal disclaimer.

(21) Appl. No.: 10/997,293

(22) Filed: Nov. 23, 2004

(65) Prior Publication Data

US 2005/0171430 A1    Aug. 4, 2005

Related U.S. Application Data

(63) Continuation-in-part of application No. 10/305,936, filed on Nov. 27, 2002, which is a continuation-in-part of application No. 10/160,836, filed on May 31, 2002, which is a continuation-in-part of application No. PCT/US01/43237, filed on Nov. 19, 2001.

(60) Provisional application No. 60/252,946, filed on Nov. 24, 2000, provisional application No. 60/525,640, filed on Nov. 28, 2003, provisional application No. 60/577,326, filed on Jun. 4, 2004, provisional application No. 60/577,388, filed on Jun. 4, 2004.

(51) Int. Cl.
*A61B 8/00* (2006.01)

(52) U.S. Cl. .................. 600/437; 600/443; 600/444; 600/461; 382/128

(58) Field of Classification Search ......... 600/437–461; 382/128, 132, 284, 294

See application file for complete search history.

(56) References Cited

U.S. PATENT DOCUMENTS 3,556,081 A    1/1971    Jones (Continued)

FOREIGN PATENT DOCUMENTS

DE    19753571 A1    6/1999

(Continued)

OTHER PUBLICATIONS

Dec. 28, 2005 International Search Report and Written Opinion in connection with International Appl. No. PCT/US05/19604.

(Continued)

*Primary Examiner*—Long V Le
*Assistant Examiner*—Sanjay Cattungal
(74) *Attorney, Agent, or Firm*—Cooper & Dunham, LLP

(57) ABSTRACT

Displaying breast ultrasound information on an interactive user interface is described, the user interface being useful in adjunctive ultrasound mammography environments and/or ultrasound-only mammography environments. Bilateral comparison is facilitated by a pairwise display of thick-slice images corresponding to analogous slab-like subvolumes in the left and right breasts. Coronal thick-slice imaging and convenient navigation on and among coronal thick-slice images is described. In one preferred embodiment, a nipple marker is displayed the coronal thick-slice image representing a projection of a nipple location thereupon. A convenient breast icon is also displayed including a cursor position indicator variably disposed thereon in a manner that reflects a relative position between the cursor and the nipple marker. Preferably, the breast icon is configured to at least roughly resemble a clock face, the center of the clock face representing the nipple marker location. Bookmark-centric and CAD-marker-centric navigation within and among thick-slice images is also described.

36 Claims, 21 Drawing Sheets

U.S. PATENT DOCUMENTS

| | | | |
|---|---|---|---|
| 3,765,403 A | 10/1973 | Brenden | |
| 4,167,180 A | 9/1979 | Kossoff | |
| 4,282,880 A | 8/1981 | Gardineer et al. | |
| 4,298,009 A | 11/1981 | Mezrich et al. | |
| 4,478,084 A * | 10/1984 | Hassler et al. | 73/620 |
| 4,485,819 A | 12/1984 | Igl | |
| 4,722,345 A | 2/1988 | Ueno et al. | |
| 4,729,019 A | 3/1988 | Rouvrais | |
| 4,796,632 A | 1/1989 | Boyd et al. | |
| 4,930,143 A | 5/1990 | Lundgren et al. | |
| 5,078,142 A | 1/1992 | Siczek et al. | |
| 5,079,698 A | 1/1992 | Grenier et al. | |
| 5,099,848 A * | 3/1992 | Parker et al. | 600/443 |
| 5,133,020 A | 7/1992 | Giger et al. | |
| 5,346,057 A | 9/1994 | Fisher et al. | |
| 5,379,769 A | 1/1995 | Ito et al. | |
| 5,396,890 A | 3/1995 | Weng | |
| 5,413,211 A | 5/1995 | Faulkner | |
| 5,433,202 A | 7/1995 | Mitchell et al. | |
| 5,479,927 A * | 1/1996 | Shmulewitz | 600/445 |
| 5,488,952 A | 2/1996 | Schoolman | |
| 5,491,627 A | 2/1996 | Zhang et al. | |
| 5,503,152 A | 4/1996 | Oakley et al. | |
| 5,511,026 A | 4/1996 | Cleveland et al. | |
| 5,603,326 A | 2/1997 | Richter | |
| 5,640,956 A | 6/1997 | Getzinger et al. | |
| 5,660,185 A | 8/1997 | Schmulewitz et al. | |
| 5,662,109 A | 9/1997 | Hutson | |
| 5,664,573 A | 9/1997 | Shmulewitz | |
| 5,671,294 A | 9/1997 | Rogers et al. | |
| 5,673,332 A | 9/1997 | Nishikawa et al. | |
| 5,709,206 A | 1/1998 | Teboul | |
| 5,729,620 A | 3/1998 | Wang | |
| 5,734,384 A | 3/1998 | Yanof et al. | |
| 5,776,062 A | 7/1998 | Nields | |
| 5,779,641 A | 7/1998 | Hatfield et al. | |
| 5,790,690 A | 8/1998 | Doi et al. | |
| 5,803,082 A | 9/1998 | Stapleton et al. | |
| 5,815,591 A | 9/1998 | Roehrig et al. | |
| 5,820,552 A | 10/1998 | Crosby et al. | |
| 5,828,774 A | 10/1998 | Wang | |
| 5,833,627 A | 11/1998 | Shmulewitz et al. | |
| 5,840,032 A | 11/1998 | Hatfield et al. | |
| 5,851,180 A | 12/1998 | Crosby et al. | |
| 5,865,750 A | 2/1999 | Hatfield et al. | |
| 5,899,863 A | 5/1999 | Hatfield et al. | |
| 5,904,653 A | 5/1999 | Hatfield et al. | |
| 5,917,929 A | 6/1999 | Marshall et al. | |
| 5,919,139 A | 7/1999 | Lin | |
| 5,934,288 A | 8/1999 | Avila et al. | |
| 5,935,071 A | 8/1999 | Schneider et al. | |
| 5,938,613 A | 8/1999 | Shmulewitz et al. | |
| 5,954,650 A | 9/1999 | Saito et al. | |
| 5,964,707 A | 10/1999 | Fenster et al. | |
| 5,983,123 A | 11/1999 | Schmulewitz | |
| 5,984,870 A * | 11/1999 | Giger et al. | 600/443 |
| 5,997,477 A | 12/1999 | Sehgal | |
| 6,027,457 A | 2/2000 | Shmulewitz et al. | |
| 6,029,797 A | 2/2000 | Olsson | |
| 6,035,056 A | 3/2000 | Karssemeijer | |
| 6,059,727 A * | 5/2000 | Fowlkes et al. | 600/443 |
| 6,068,597 A | 5/2000 | Lin | |
| 6,075,879 A | 6/2000 | Roehrig et al. | |
| 6,091,841 A | 7/2000 | Rogers et al. | |
| 6,102,861 A | 8/2000 | Avila et al. | |
| 6,102,866 A | 8/2000 | Nields et al. | |
| 6,117,080 A | 9/2000 | Schwartz | |
| 6,155,978 A | 12/2000 | Cline et al. | |
| 6,157,697 A | 12/2000 | Mertelmeier et al. | |
| 6,178,224 B1 | 1/2001 | Policher et al. | |
| 6,181,769 B1 | 1/2001 | Hoheisel et al. | |
| 6,190,334 B1 * | 2/2001 | Lasky et al. | 600/587 |
| 6,198,838 B1 | 3/2001 | Roehrig et al. | |
| 6,237,750 B1 | 5/2001 | Damkjaer et al. | |
| 6,246,782 B1 * | 6/2001 | Shapiro et al. | 382/128 |
| 6,254,538 B1 | 7/2001 | Downey et al. | |
| 6,263,092 B1 | 7/2001 | Roehrig et al. | |
| 6,266,435 B1 | 7/2001 | Wang | |
| 6,269,565 B1 | 8/2001 | Inbar et al. | |
| 6,278,793 B1 | 8/2001 | Gur et al. | |
| 6,282,305 B1 | 8/2001 | Huo et al. | |
| 6,301,378 B1 | 10/2001 | Karssemeijer et al. | |
| 6,311,419 B1 | 11/2001 | Inbar | |
| 6,317,617 B1 | 11/2001 | Gilhuijs et al. | |
| 6,334,847 B1 * | 1/2002 | Fenster et al. | 600/443 |
| 6,377,838 B1 | 4/2002 | Iwanczyk et al. | |
| 6,385,474 B1 | 5/2002 | Rather et al. | |
| 6,396,940 B1 * | 5/2002 | Carrott et al. | 382/128 |
| 6,413,219 B1 | 7/2002 | Avila et al. | |
| 6,450,962 B1 * | 9/2002 | Brandl et al. | 600/458 |
| 6,459,925 B1 * | 10/2002 | Nields et al. | 600/427 |
| 6,461,298 B1 | 10/2002 | Fenster et al. | |
| 6,524,246 B1 | 2/2003 | Kelly et al. | |
| 6,530,885 B1 * | 3/2003 | Entrekin et al. | 600/437 |
| 6,574,499 B1 * | 6/2003 | Dines et al. | 600/427 |
| 6,628,815 B2 * | 9/2003 | Wang | 382/132 |
| 6,630,937 B2 * | 10/2003 | Kallergi et al. | 345/619 |
| 6,636,584 B2 | 10/2003 | Johnson et al. | |
| 6,682,484 B1 | 1/2004 | Entrekin et al. | |
| 6,876,879 B2 | 4/2005 | Dines et al. | |
| 6,909,792 B1 * | 6/2005 | Carrott et al. | 382/128 |
| 2002/0173722 A1 | 11/2002 | Hoctor et al. | |
| 2003/0000810 A1 | 1/2003 | Hansen et al. | |
| 2003/0015406 A1 | 1/2003 | Guldenfels et al. | |
| 2003/0181801 A1 | 9/2003 | Lasser et al. | |
| 2003/0194121 A1 * | 10/2003 | Eberhard et al. | 382/132 |
| 2004/0015080 A1 | 1/2004 | Kelly et al. | |
| 2004/0181152 A1 | 9/2004 | Zhang | |
| 2004/0254464 A1 | 12/2004 | Stribling | |
| 2005/0113683 A1 | 5/2005 | Lokhandwalla et al. | |

FOREIGN PATENT DOCUMENTS

| | | |
|---|---|---|
| DE | 19902521 A1 | 7/2000 |
| JP | 2003310614 | 11/2003 |
| WO | WO 8302053 A1 | 6/1983 |
| WO | WO 03103500 A1 | 12/2003 |
| WO | WO 2004/064644 A1 | 8/2004 |

OTHER PUBLICATIONS

Foster F. S. et al. "The Ultrasound Macroscope: Initial Studies of Breast Tissue" Ultrasonic Imaging USA, vol. 6, No. 3, Jul. 1984, pp. 243-261.

European Search Report dated Jan. 29, 2007 in connection with European patent application No. 03 73 4336.

Russ, "The Image Processing Handbook, $3^{rd}$ Edition", CRC Press/IEEE Press, p. 264, 1998.

* cited by examiner

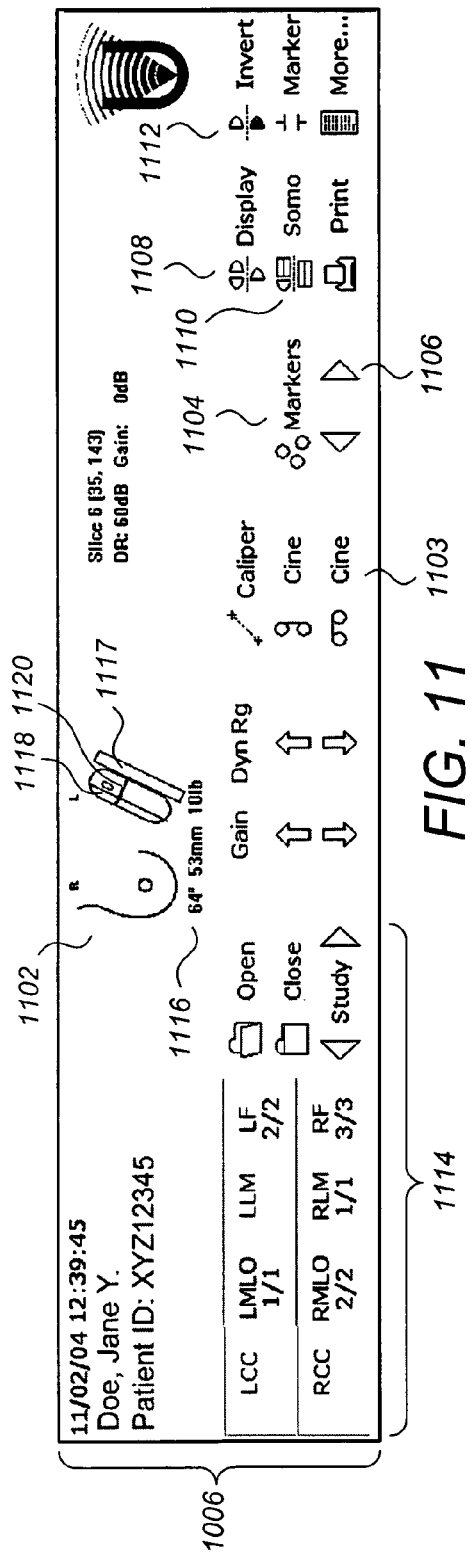
FIG. 11
FIG. 12
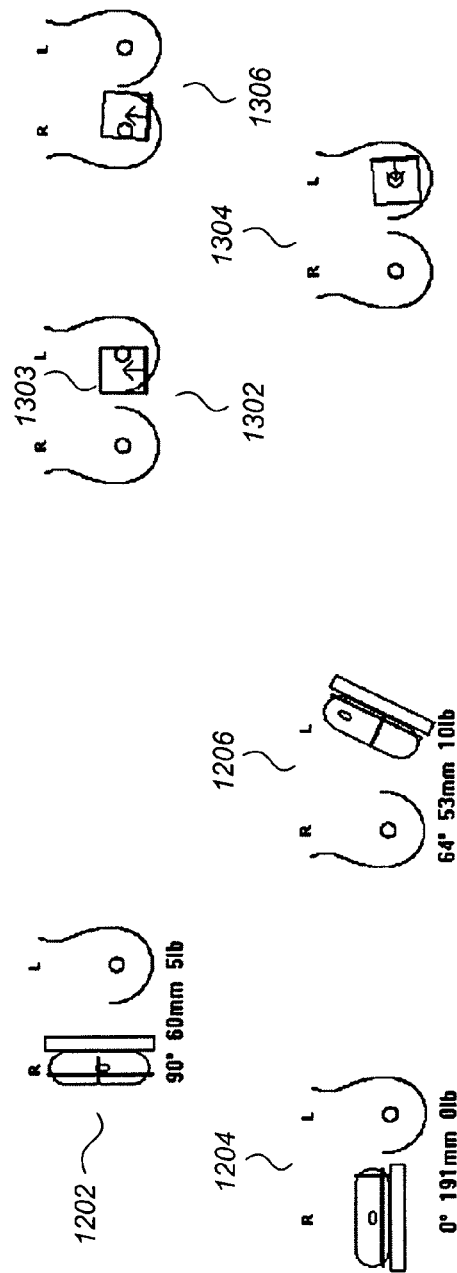
FIG. 13

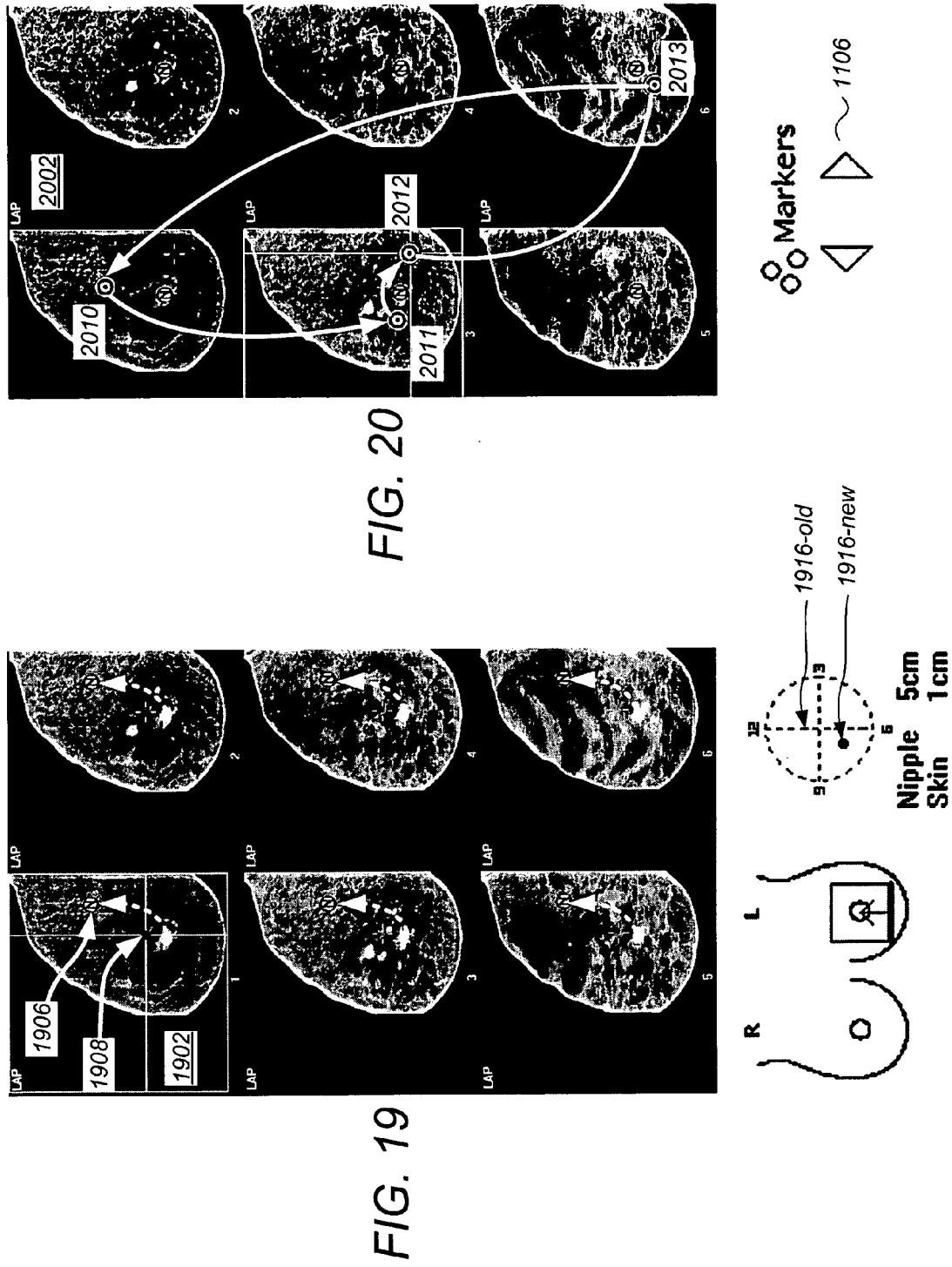

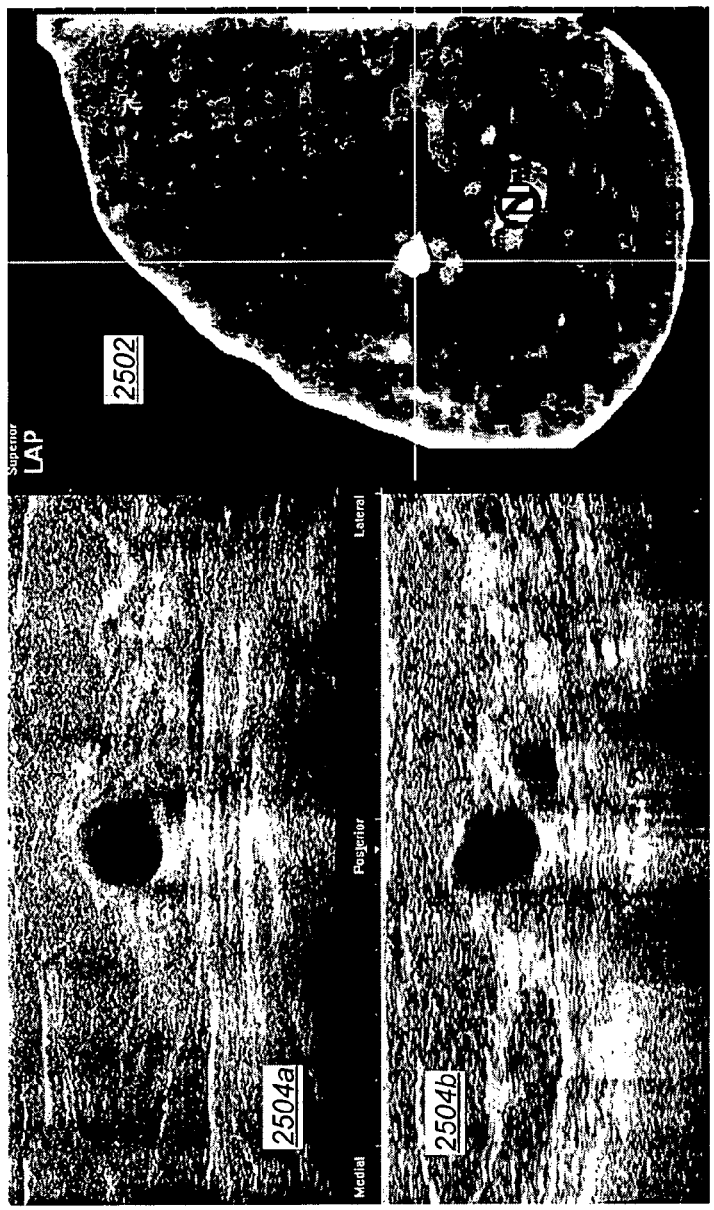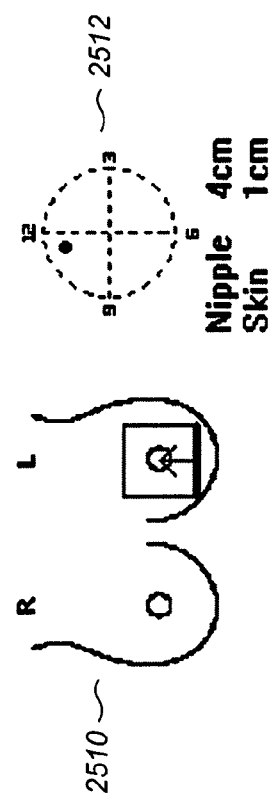
FIG. 25

PROCESSING AND DISPLAYING BREAST ULTRASOUND INFORMATION

CROSS-REFERENCE TO RELATED APPLICATIONS

This application is a continuation-in-part of U.S. Ser. No. 10/305,936, filed Nov. 27, 2002, which is a continuation-in-part of U.S. Ser. No. 10/160,836, filed May 31, 2002, which is a continuation-in-part of International Application Ser. No. PCT/US01/43237, filed Nov. 19, 2000, which claims the benefit of U.S. Provisional Application No. 60/252,946, filed Nov. 24, 2000, each of these applications being incorporated by reference herein. This application claims the benefit of Provisional Application No. 60/525,640, filed Nov. 28, 2003, Provisional Application No. 60/577,326, filed Jun. 4, 2004, and Provisional Application No. 60/577,388, filed Jun. 4, 2004, each of these applications also being incorporated by reference herein.

FIELD

This patent specification relates to medical ultrasound imaging. More particularly, this patent specification relates to processing and/or display of breast ultrasound information for breast cancer screening and/or diagnosis purposes.

BACKGROUND

Volumetric ultrasound scanning of the breast can serve as a complementary modality for breast cancer screening as described, for example, in the commonly assigned US 2003/0007598A1 and US 2003/0212327A1, each of which is incorporated by reference herein. Whereas a conventional two-dimensional x-ray mammogram only detects a summation of the x-ray opacity of individual slices of breast tissue over the entire breast, ultrasound can separately detect the sonographic properties of individual slices of breast tissue, and therefore may allow detection of breast lesions where x-ray mammography alone fails. Another well-known shortcoming of x-ray mammography practice is found in the case of dense-breasted women, including patients with high content of fibroglandular tissues in their breasts. Because fibroglandular tissues ha+ve higher x-ray absorption than the surrounding fatty tissues, portions of breasts with high fibroglandular tissue content are not well penetrated by x-rays and thus the resulting mammograms contain reduced information in areas where fibroglandular tissues reside. Still another shortcoming of x-ray mammography practice relates to difficulty in imaging near the chest wall, because it is difficult to extend these tissues outward onto the compression plates for proper imaging. A substantial number of cancers are known to occur within 3 cm of the chest wall, which can thereby be missed by x-ray mammography.

In addition to being useful as a complementary modality to x-ray mammography, ultrasound mammography could well become a sole breast cancer screening modality for at least some patient groups. For example, it is believed that preventive health care policy will progress toward the adoption of regular breast cancer screening procedures for increasingly younger women, e.g., women under the age of 40, and perhaps even under the age of 30 if there is a family history of cancer. Because younger women generally have denser breasts, the shortcomings of conventional two-dimensional x-ray mammography are expected to become especially apparent. Even further, because the dangers of x-ray radiation exposure are cumulative over a lifetime, ultrasound mammography could well become a sole breast cancer screening modality for women in these younger age groups. Other demographics indicating higher breast densities among certain groups, regions, or countries may also lead to the increased adoption of breast ultrasound as a sole or adjunctive screening modality for those groups, regions, or countries.

Once a thorough set of breast ultrasound scans is obtained, a challenge arises in the context of processing and displaying the breast ultrasound information to a clinician. In general, there is an inherent tension between (i) promoting high sensitivity/specificity in the screening and/or diagnosis process, and (ii) promoting efficient patient throughput to keep costs manageable. Thus, for example, while careful slice-by-slice scrutiny of the raw ultrasound scans by a well-trained radiologist would promote high sensitivity and specificity, the overall workflow efficiency of this method would be low, and therefore costs would be high, in view of the hundreds of individual raw ultrasound slices to be reviewed for each patient.

Accordingly, it would be desirable to provide an interactive user interface for viewing breast ultrasound information that can be effective for (i) adjunctive ultrasound mammography environments in which the ultrasound information complements x-ray mammogram information, and/or (ii) ultrasound-only mammography environments in which ultrasound is a sole screening modality.

It would be further desirable to provide processing and display of breast ultrasound information in a manner that promotes high specificity and sensitivity in the breast cancer screening and/or diagnosis process.

It would be still further desirable to provide such processing and display of breast ultrasound information while also promoting high patient throughput and low per-patient costs in the breast cancer screening and/or diagnosis process.

It would be even further desirable to provide such processing and display of breast ultrasound information that is effective for a wide variety of breast sizes, including smaller-sized breasts.

It would be still further desirable to provide an interactive user interface for an ultrasound mammography system that allows the radiologist to quickly and intuitively navigate among different representations of the breast ultrasound information.

It would be even further desirable to provide such processing and display of breast ultrasound information that is effective in exposing breast abnormalities that are in close proximity to the chest wall of the patient, where a comparatively high percentage of breast abnormalities arise.

SUMMARY

A system, method, and computer program product for processing and displaying breast ultrasound information is provided, wherein a plurality of two-dimensional coronal thick-slice images are generated from a three-dimensional data volume of a sonographic property of a breast, each coronal thick-slice image representing the sonographic property within a slab-like subvolume of the breast substantially parallel to a coronal plane. The coronal thick-slice images are displayed to a viewer, such as a clinician, on a user display. In one preferred embodiment, the plurality of coronal thick-slice images collectively represent the entire breast volume, and are displayed simultaneously.

Advantageously, the array of coronal thick-slice images includes one or more members corresponding to subvolumes abutting the chest wall, which allows for detailed visual review of tissue structures near the chest wall. Preferably, the three-dimensional data volume has been obtained while the breast was compressed in a chestward direction and scanned using a high frequency ultrasound probe, which allows for high resolution in the coronal thick-slice images. However, the scope of the preferred embodiments is not so limited, and in other preferred embodiments the breast may have been scanned while uncompressed or while compressed along other orientations.

In another preferred embodiment, a plurality of two-dimensional standard-plane thick-slice images are generated from the three-dimensional data volume, the standard-plane thick-slice images corresponding to slab-like subvolumes substantially parallel to a standard x-ray mammogram view plane, such as the craniocaudal (CC) or the mediolateral oblique (MLO) view plane. The standard-plane thick-slice images are then displaying along with the coronal thick-slice images on the user display, preferably in a side-by-side presentation so that all are simultaneously visible. In another preferred embodiment, conventional x-ray mammogram images are also displayed alongside the thick-slice ultrasound images.

In one preferred embodiment, all of the slab-like subvolumes corresponding to the coronal thick-slice images have the same thickness. In an alternative preferred embodiment, an average thickness of a first subset of the slab-like subvolumes located closer to the chest wall is less than an average thickness of a second subset of said slab-like subvolumes located farther from the chest wall, whereby detection of smaller structures nearer to the chest wall is facilitated while avoiding the presentation of "too much information" to the viewing clinician. Alternatively or in conjunction therewith, the three-dimensional data volume is processed according to at least one computer-aided detection (CAD) algorithm to detect anatomical abnormalities (e.g., spiculated mass lesions, microcalcifications, etc.) in the breast, and the coronal thick-slice images are correspondingly annotated on the user display.

In another preferred embodiment, a method, apparatus, and related computer program products for displaying breast ultrasound information are provided including an interactive user interface that can be used in adjunctive ultrasound mammography environments and/or ultrasound-only mammography environments. According to a preferred embodiment, bilateral comparison is facilitated by displaying a first thick-slice image representing a sonographic property within a first slab-like subvolume of a first breast of a patient, and displaying a second thick-slice image adjacent to the first thick-slice image. The second thick-slice image represents the sonographic property within a second slab-like subvolume of a second breast opposite the first breast, the first and second slab-like subvolumes occupying generally similar positions within the first and second breasts, respectively.

According to another preferred embodiment, a thick-slice image representing a sonographic property of a breast within a slab-like subvolume thereof is displayed, wherein the slab-like subvolume has a thickness between 2 mm and 20 mm, and wherein the slab-like subvolume is substantially parallel to a coronal plane. The thick-slice image may be a member of a thick-slice image array corresponding to successive slab-like subvolumes within the breast substantially parallel to the coronal plane, a plurality of which can be simultaneously displayed for a quick overview of the internal breast tissue.

In another preferred embodiment, a single composite thick-slice image corresponding to the entire breast volume is displayed. Preferably, the composite thick-slice image is enhanced according at least one computer-aided detection (CAD) algorithm operating on the acquired three-dimensional breast volume.

In another preferred embodiment, a thick-slice image is displayed on a display monitor, the thick-slice image representing a sonographic property of a breast within a slab-like subvolume thereof, the slab-like subvolume being substantially parallel to a coronal plane. A nipple marker is displayed on the thick-slice image representing a projection of a nipple location onto that thick-slice image. A cursor is also displayed upon the thick-slice image according to a viewer manipulation of a pointing device associated with the display monitor. To facilitate easy and intuitive navigation and viewing, a breast icon is displayed near the thick-slice image, the breast icon including a cursor position indicator that is movably disposed thereon in a manner that reflects a relative current position between the cursor and the nipple marker on the thick-slice image. Preferably, the breast icon is configured to at least roughly resemble a clock face, and the center of that clock face represents the nipple marker position, i.e., the cursor position indicator is placed relative to the center of the clock face in a manner that reflects the current position of the cursor on the thick-slice image relative to the nipple marker.

To further facilitate quick and intuitive viewing, a bookmarking capability is provided that allows the viewer to place bookmarks upon the thick-slice images as well as upon any planar ultrasound images being displayed. Advantageously, a bookmark-centric navigation capability is provided that allows the viewer to promptly proceed precisely to the next bookmark on the thick-slice image(s), as well as to cause the planar ultrasound image(s) to promptly correspond to that next bookmark location. Alternatively or in conjunction therewith, a computer-aided diagnosis (CAD)-centric navigation capability is provided that allows the viewer to proceed promptly among CAD detections, i.e., locations that may be suspicious as determined by a computer-aided diagnosis system, on both the thick-slice and planar ultrasound images.

BRIEF DESCRIPTION OF THE DRAWINGS

FIG. 11 illustrates a menu bar of a breast ultrasound display according to a preferred embodiment;

FIGS. 12 and 13 illustrate body marker icons according to a preferred embodiment;

FIG. 19 illustrates an array of thick-slice images with viewer-shifted nipple markers, a body marker icon, and a frontal breast icon according to a preferred embodiment;

FIG. 20 illustrates an array of thick-slice images with nipple markers and bookmarks, a marker display button, and marker navigation buttons according to a preferred embodiment;

FIG. 25 illustrates a full-breast composite thick-slice image, a body marker icon, and a frontal breast icon according to a preferred embodiment.

DETAILED DESCRIPTION

Figure 1:
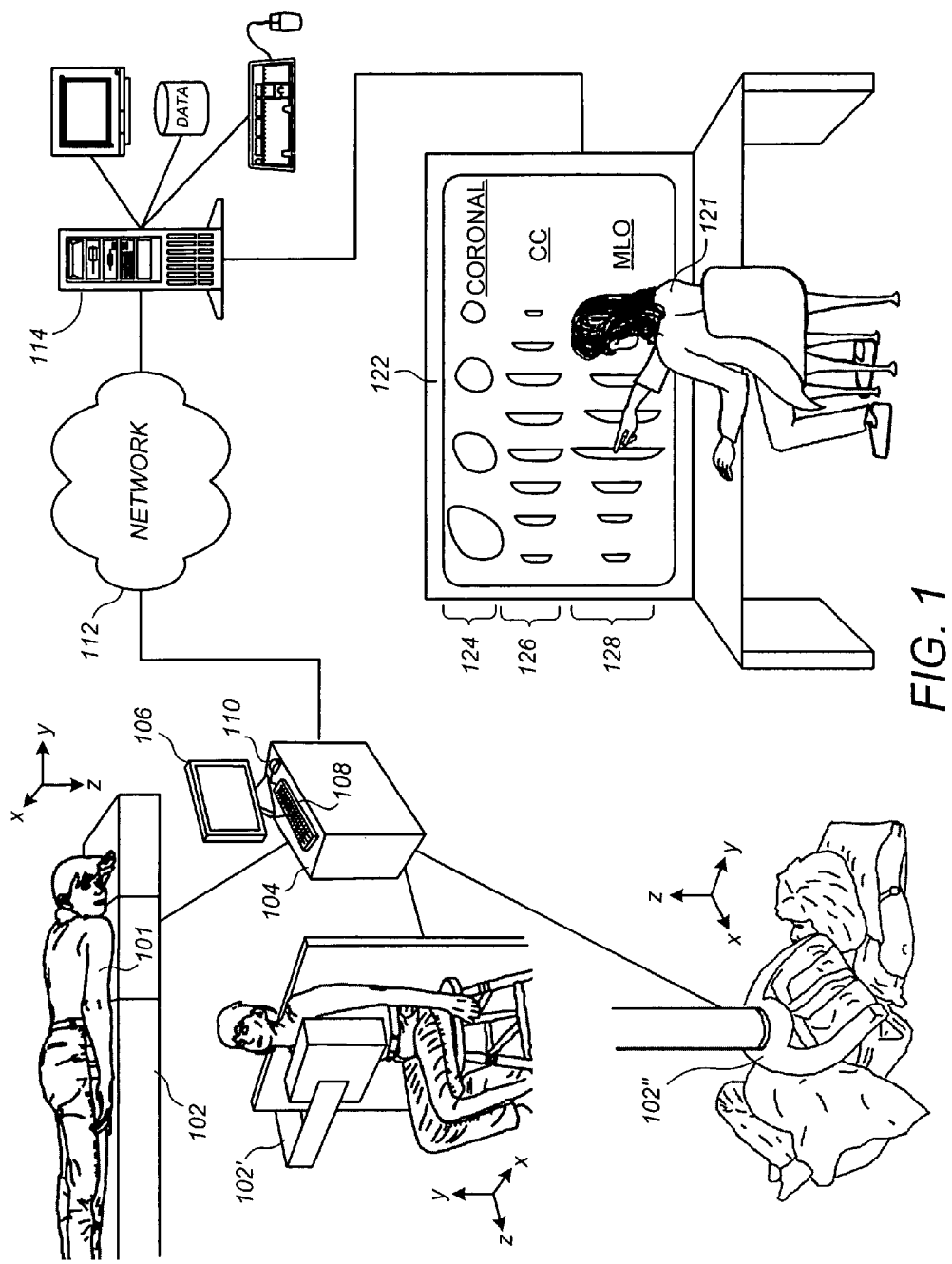
FIG. 1 illustrates a conceptual diagram of a breast cancer screening and/or diagnosis system according to a preferred embodiment.

FIG. 1 illustrates a conceptual diagram of a breast cancer screening and/or diagnosis system according to a preferred embodiment. The breast of a patient 101 is ultrasonically scanned by an automated scanning apparatus while the patient is in a prone position (device 102), an upright position (device 102'), a supine position (device 102") or other position (not shown). By reducing the required ultrasonic penetration depth to the chest wall, scanning of a chestwardly compressed breast can occur at higher frequencies, e.g., 10-20 MHz, which can yield very high resolution images sufficient to facilitate detection of microcalcifications or other structures on the order of 1 mm near the chest wall. However, it is to be appreciated that the scope of the preferred embodiments is not limited to a chestwardly-compressed scenario, with breast ultrasound information processing and display according to the preferred embodiments being generally useful with any scanning system from which a three-dimensional volumetric representation of a sonographic property of the breast can be derived.

Breast scans are obtained under the control of a scanning engine and workstation 104 including, for example, a monitor 106, keyboard 108, a mouse 110, and a scanning engine (not shown). During or after the scanning process, the ultrasound scan data is provided across a computer network 112 to an ultrasound server 114 that processes and generates display information according to the functionalities described herein. The ultrasound server 114 may perform other HIS/RIS (hospital information system/radiology information system) activities such as archiving, scheduling, etc. It is to be appreciated that the processing of the ultrasound scan data may be performed by any of a variety of different computing devices coupled to the computer network 112 in various combinations without departing from the scope of the preferred embodiments.

According to a preferred embodiment, a viewing workstation 122 is provided that displays an array 124 of coronal thick-slice images to a clinician 121, each coronal thick-slice image representing a sonographic property of the breast within a slab-like subvolume thereof substantially parallel to a coronal plane. As used herein, the term "clinician" generically refers to a medical professional, such as a radiologist, or other person that analyzes medical images and makes clinical determinations therefrom, it being understood that such person might be titled differently, or might have varying qualifications, depending on the country or locality of their particular medical environment. In another preferred embodiment, as shown in FIG. 1, one or more standard-plane thick slice image arrays are displayed to the clinician 121, such as a craniocaudal (CC) thick-slice image array 126 and a mediolateral oblique (MLO) thick-slice image array 128.

In another preferred embodiment (not shown), the clinician is also provided with the ability to view individual planar ultrasound slices (along sagittal, axial, coronal, or other cut-planes through the three-dimensional breast volume) as desired. An example of one desirable planar ultrasound display and navigation scheme is provided in the commonly assigned US2003/0212327A1, supra, and in other preferred embodiments described herein.

Figure 2:
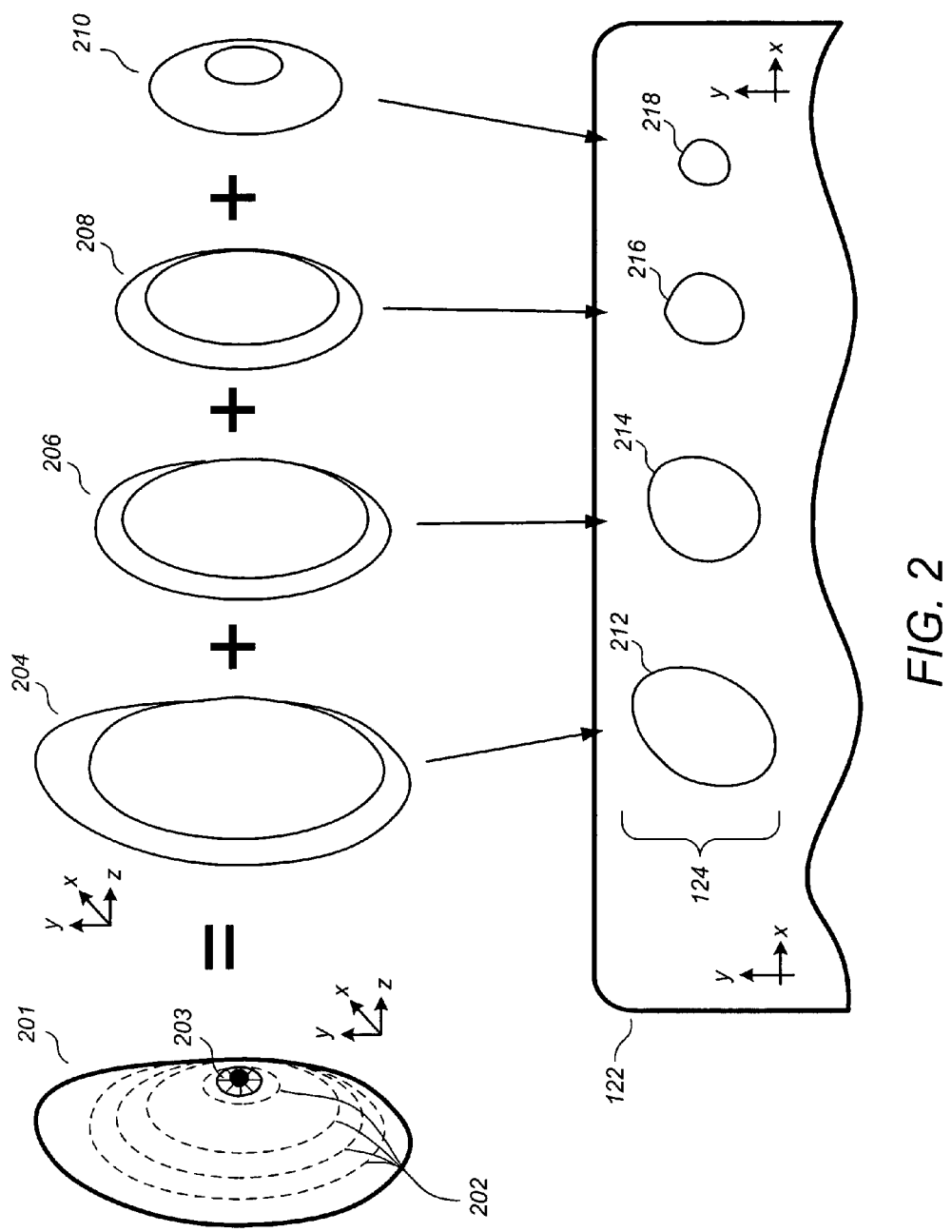
FIG. 2 illustrates a perspective view of a breast volume and slab-like subvolumes thereof substantially parallel to a coronal plane, and an array of two-dimensional coronal thick-slice images corresponding thereto.

FIG. 2 illustrates a perspective view of a breast volume 201 and coronal slab-like subvolumes 204-210 thereof substantially parallel to a coronal plane, along with the array 124 of two-dimensional coronal thick-slice images generated therefrom according to a preferred embodiment. The coronal slab-like subvolumes 204-210, which are separated by planes 202, correspond to the coronal thick-slice images 212-218, respectively. Generally speaking, the coronal slab-like subvolumes nearer to the chest wall (e.g., 204-206) have a larger cross-section in the coronal plane than the slab-like subvolumes nearer to the nipple 203 (e.g., 208-210). As used herein, coronal slab-like subvolumes refer generally to slab-like subvolumes within the breast that are roughly parallel to the chest wall of the patient. The coronal slab-like subvolumes 204-210 typically have a thickness in the range of 2-20 mm. Optionally, the coronal slab-like subvolumes can be gently contoured to more closely follow the contours of the chest wall. In such cases, the coronal slab-like subvolumes would have surfaces roughly reminiscent of a section of a hyperboloid, or roughly reminiscent of a potato chip.

Generally speaking, a coronal thick-slice image comprises an integration of a plurality of individual ultrasound slices lying within a coronal slab-like subvolume. Thus, for example, where the coronal slab-like subvolume 204 is represented by a three-dimensional voxel array V(x,y,z) of scalar values, the corresponding coronal thick-slice image 212 would be a two-dimensional pixel array $P_{COR}(x,y)$ of scalar values. in one preferred embodiment, each pixel value $P_{COR}(x,y)$ is simply computed as an arithmetic average along the corresponding voxel column at (x,y) having the voxel values $V(x,y,z_0), V(x,y,z_1), V(x,y,z_2), \ldots, V(x,y,z_N)$, where N is the number of individual ultrasound slices lying in the coronal slab-like subvolume. For clarity of description, the voxel column at (x,y) having the voxel values $V(x,y,z_0)$, $V(x,y,z_1), V(x,y,z_2), \ldots, V(x,y,z_N)$ is expressed herein as $V_{xy}(z)$.

Techniques for integrating the component ultrasound slices into the coronal thick-slice images $P_{COR}(x,y)$ according to the preferred embodiments include arithmetic averaging, geometric averaging, reciprocal averaging, exponential averaging, and other averaging methods, in each case including both weighted and unweighted averaging techniques. Other suitable integration methods may be based on statistical properties of the population of component ultrasound slices at common locations, such as maximum value, minimum value, mean, variance, or other statistical algorithms.

Preferably, the coronal slab-like subvolumes have a thickness related to the size of the lesions to be detected. At an upper end, a larger thickness of 20 mm, for example, may be used if it is desirable to overlook most of the breast details and direct the user's attention to larger features on the order 10 mm in size. At a lower end, a smaller thickness of 2 mm, for example, may be used if it is desirable to view small structures, such as microcalcifications, on the order of 1 mm in size. Thicknesses in the range of 4 mm-10 mm are likely to be suitable for most breast cancer screening purposes.

In other preferred embodiments, the pixel value $P_{COR}(x,y)$ may be computed according to an algorithm that processes a neighborhood of voxel columns around the voxel column $V_{xy}(z)$, the algorithm being designed to result in coronal thick-slice images that emphasize lesions of a predetermined size range. In one such preferred embodiment, the integration method comprises weighting the voxels of the corresponding voxel column by a weighting vector and then summing the results, the weighting vector being computed according to neighborhood characteristics around that voxel column. This can be summarized by Eq. (1) below:

$$P_{COR}(x, y) = FUNC\{V_{xy}(z)\} = \sum_{n=1}^{N} W_{xy}(n) V_{xy}(z_n) \quad \{1\}$$

Using known three-dimensional segmentation and computer-aided detection (CAD) techniques, the locations and sizes of lesions in the coronal thick-slice volume are identified, either directly or by way of a mapping from the overall three-dimensional breast volume. Any of a variety of known three-dimensional segmentation and/or CAD algorithms can be used such as those discussed in U.S. Pat. No. 6,317,617 to Gilhuijs, Giger, and Bick, which is incorporated by reference herein. In one preferred embodiment, for a given voxel column, the weighting vector $W_{xy}(n)$ comprises peaks at locations lying within the lesions and valleys elsewhere, thus causing the resulting coronal thick-slice image to emphasize mass lesions in the output. In another preferred embodiment, the weighting vector $W_{xy}(n)$ can be computed as described in the commonly assigned WO 02/101303A1, which is incorporated by reference herein. The CAD-detected abnormalities can include microcalcifications, suspicious masses, and/or other known breast abnormalities.

Figure 3:
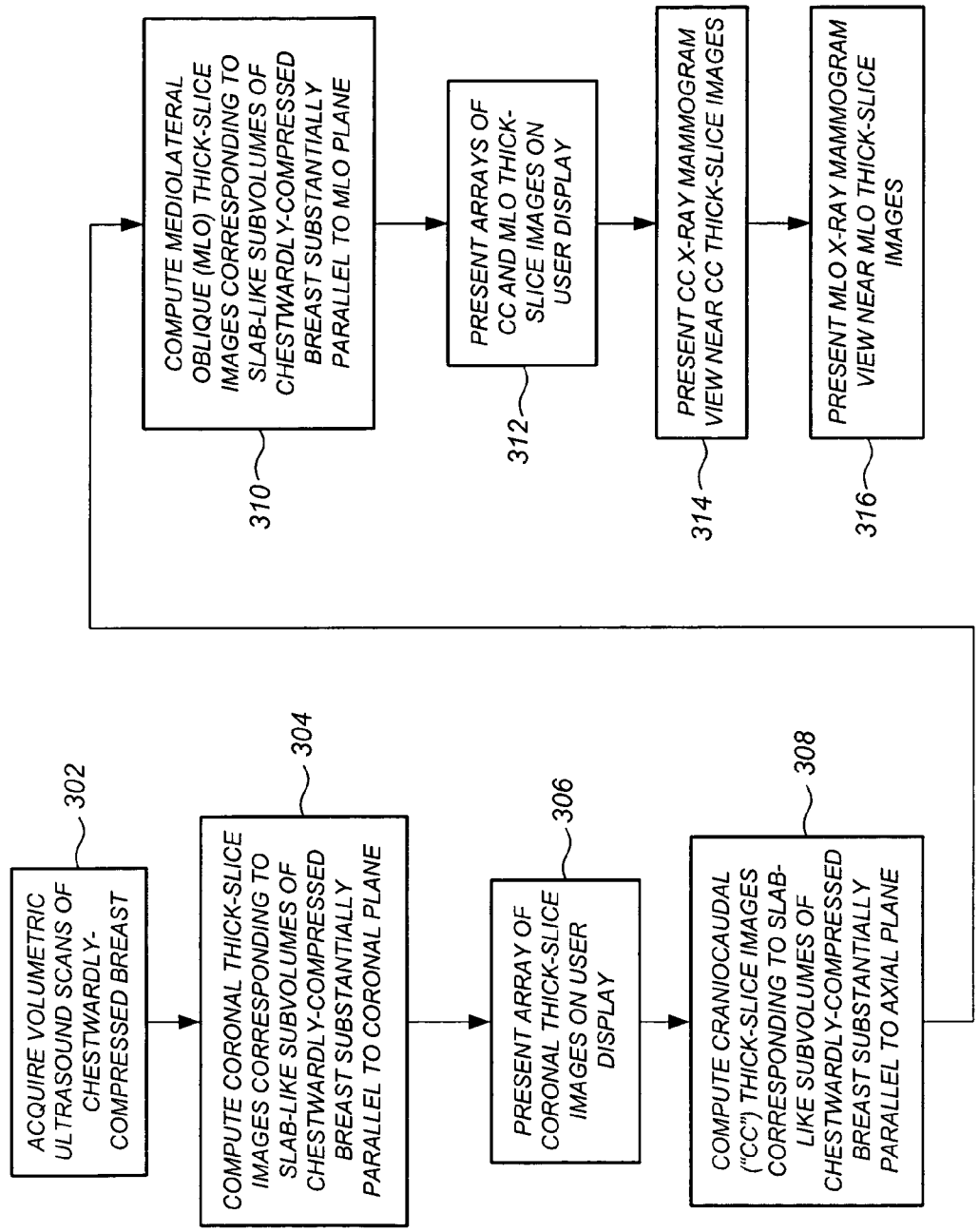
FIG. 3 illustrates a method for processing and displaying breast ultrasound information according to a preferred embodiment.

FIG. 3 illustrates a method for processing and displaying breast ultrasound information according to a preferred embodiment. At step 302, volumetric ultrasound scans of the chestwardly-compressed breast are acquired, either in real-time as the breast is being scanned, or in an off-line manner as from a database or archive of previously-acquired images. At step, 304, coronal thick-slice images are computed corresponding to slab-like subvolumes of the chestwardly-compressed breast substantially parallel to coronal plane. At step 306, the array of coronal thick-slice images is displayed on a user display, preferably in a side-by-side manner. However, a variety of different spatial arrangements of the coronal thick-slice images are within the scope of the preferred embodiments. For example, the array may be presented in circular or matrix fashion. In one preferred embodiment, all of the coronal thick-slice images collectively corresponding to the entire breast volume are simultaneously displayed to the viewer, so that the whole breast is effectively shown at the same time, thereby facilitating clinical workflow efficiency. In another preferred embodiment, the coronal thick-slice images can be progressively displayed at successive time intervals, either automatically or responsive to user controls.

According to one preferred embodiment, at step 308 craniocaudal (CC) thick-slice images, which are one type of standard-plane thick-slice image, are computed corresponding to slab-like subvolumes of the chestwardly-compressed breast substantially parallel to an axial plane, which corresponds to the CC view. At step 310 mediolateral oblique (MLO) thick-slice images, which are another type of standard-plane thick-slice image, are computed corresponding to slab-like subvolumes of the chestwardly-compressed breast substantially parallel to an MLO plane. At step 312, the arrays of CC and MLO thick-slice images are presented on the user display.

Figure 4:
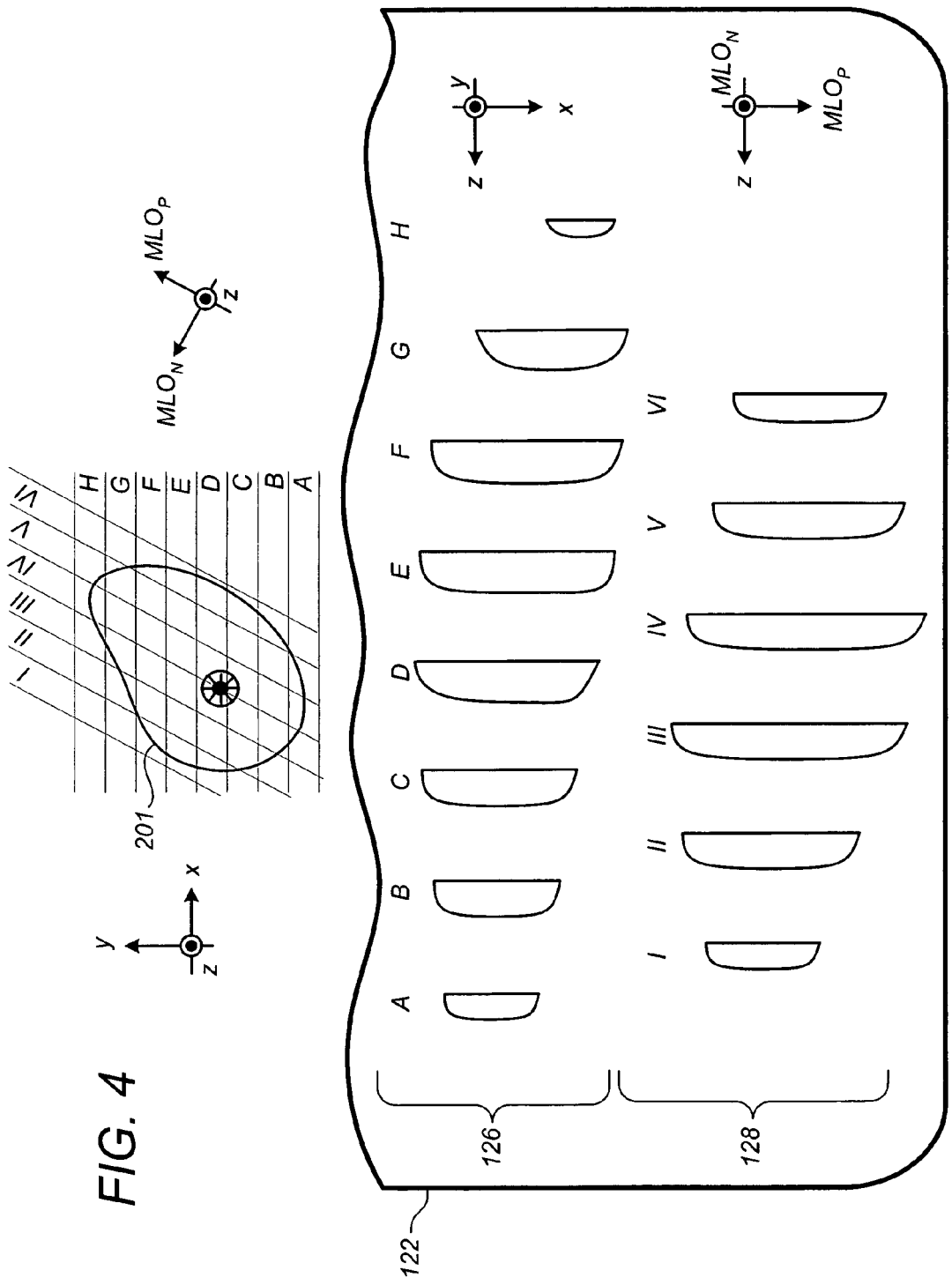
FIG. 4 illustrates a front view of a breast, a front view of slab-like subvolumes thereof substantially parallel to standard x-ray mammogram planes, and arrays of standard-plane thick-slice images corresponding thereto for display in conjunction with the coronal thick-slice images of FIG. 2 according to a preferred embodiment.

FIG. 4 illustrates a conceptual front view of the breast 201 upon which are drawn (i) front-view outlines of slab-like subvolumes A-H corresponding to CC slab-like subvolumes, and (ii) front-view outlines of slab-like subvolumes I-VI corresponding to MLO slab-like subvolumes. Also shown in FIG. 4 is a portion of the viewing workstation 122 illustrating the CC thick-slice image array 126 and the MLO thick-slice image array 128 with indicators mapping them into the slab-like subvolumes A-H and I-VI, respectively. The CC and MLO thick-slice image arrays can be generated from the three-dimensional breast volume in a manner analogous to that described in WO 02/101303A1, supra. As known in the art, the MLO plane is usually about 55 degrees away from the CC plane. It is to be appreciated, however, that a variety of angles for the MLO plane can be used without departing from the scope of the preferred embodiments, including 90 degrees (in which case it corresponds to the mediolateral "ML" view) or greater.

Figure 5:
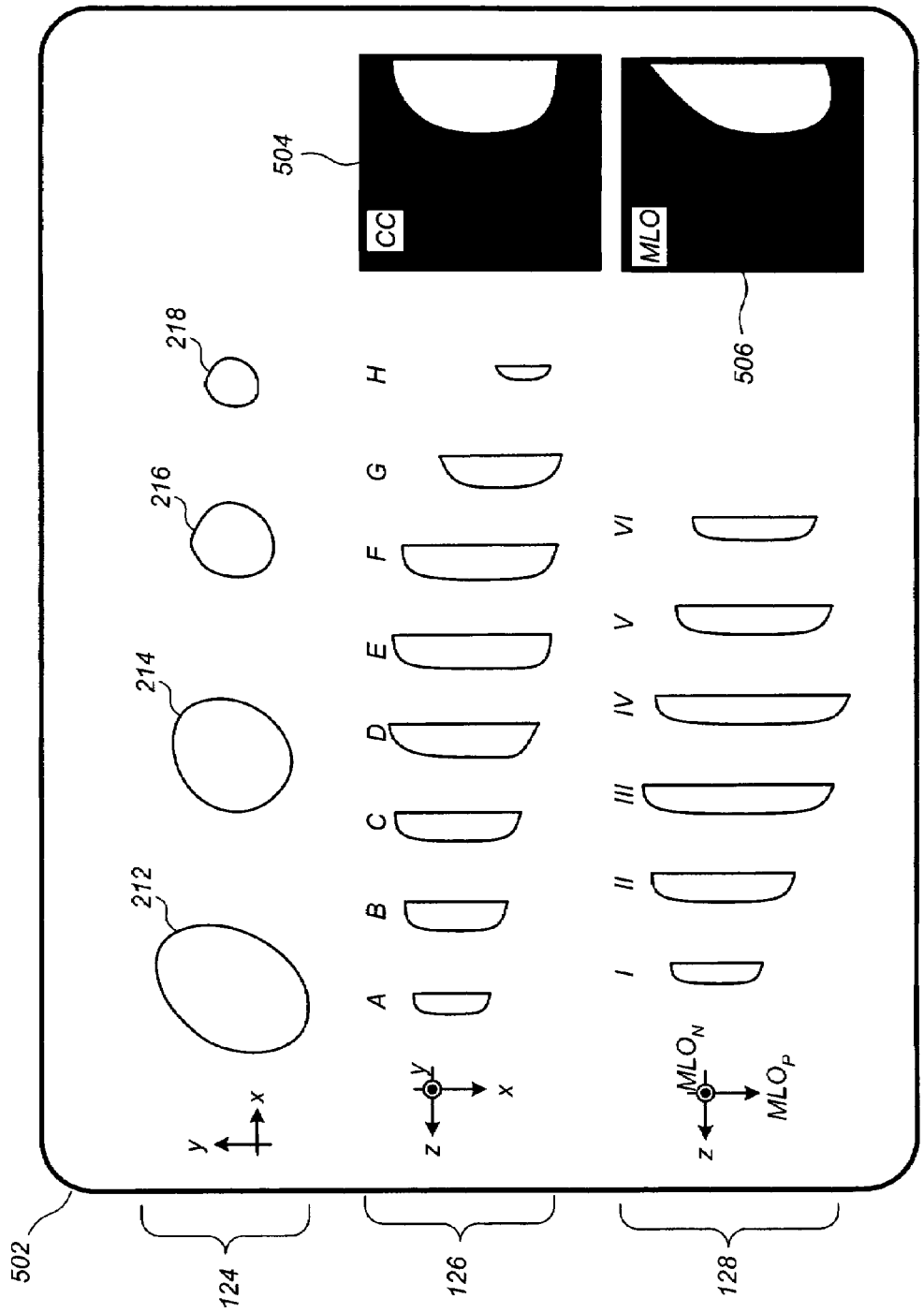
FIG. 5 illustrates a user display according to a preferred embodiment.

Referring again to FIG. 3, according to one preferred embodiment, standard CC and MLO x-ray mammogram views of the breast are displayed at steps 314 and 316, respectively. FIG. 5 illustrates a viewing workstation 502 similar to the viewing workstation 122, supra, with the addition of CC and MLO x-ray mammogram images 504 and 506, respectively, which can further facilitate screening and diagnosis through back-and-forth viewing of interesting areas. The CC and MLO x-ray mammogram images 504 and 506 are preferably in digitized form for practical reasons, although it is within the scope of the preferred embodiments for these to be film-based x-ray mammograms on a light-box background.

Figure 6A:
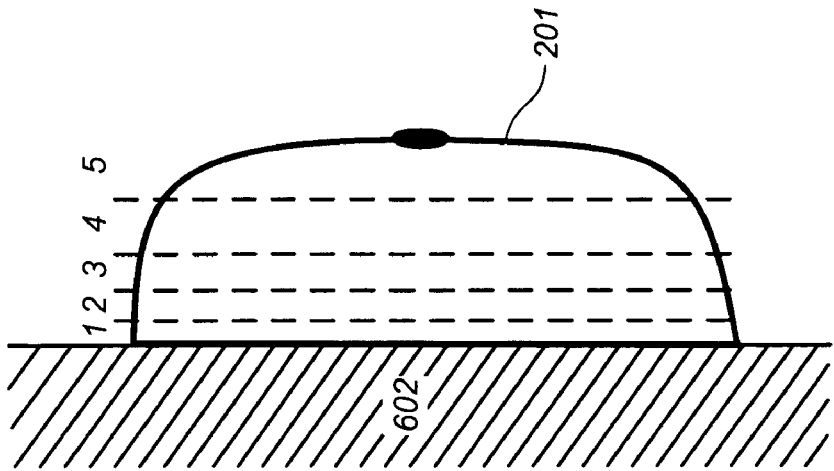
FIGS. 6A and 6B illustrate a side view of a breast and an example of different slab-like coronal subvolume thickness schemes according to a preferred embodiment.
Figure 6B:
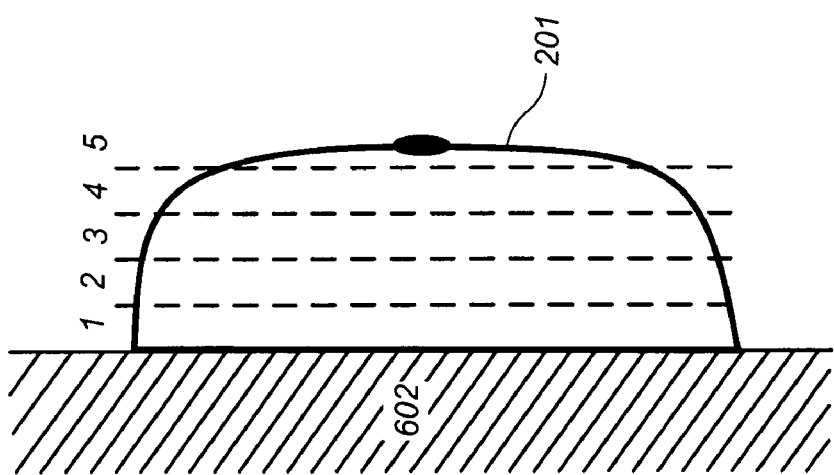

FIGS. 6A and 6B illustrate side views of a breast 201 next to a chest wall 602 for the purpose of describing coronal slab-like subvolume thickness schemes according to the preferred embodiments. In the preferred embodiment of FIG. 6A, the thicknesses of coronal slab-like subvolumes 1-5 are substantially equal. However, in the preferred embodiment of FIG. 6B, there is a graded or phased approach to the thicknesses of coronal slab-like subvolumes 1-5. More particularly, the inner subvolumes 1-2 are thinner than the outer subvolumes 4-5. Thus, an average thickness of a first subset of said slab-like subvolumes located closer to the chest wall is less than an average thickness of a second subset of said slab-like subvolumes located farther from the chest wall.

The graded or phased approach of FIG. 6B has been found advantageous because a large percentage of breast lesions are nearby to the chest wall, and so a more precise viewing of these tissues (i.e., approaching the precision of conventional thin-slice ultrasound images) is warranted. At the same time, however, it is still desirable to avoid "too much information" on the user display, and so thicker subvolumes for the regions farther away from the chest wall are used to keep the overall number of required images at manageable levels.

Figure 7:
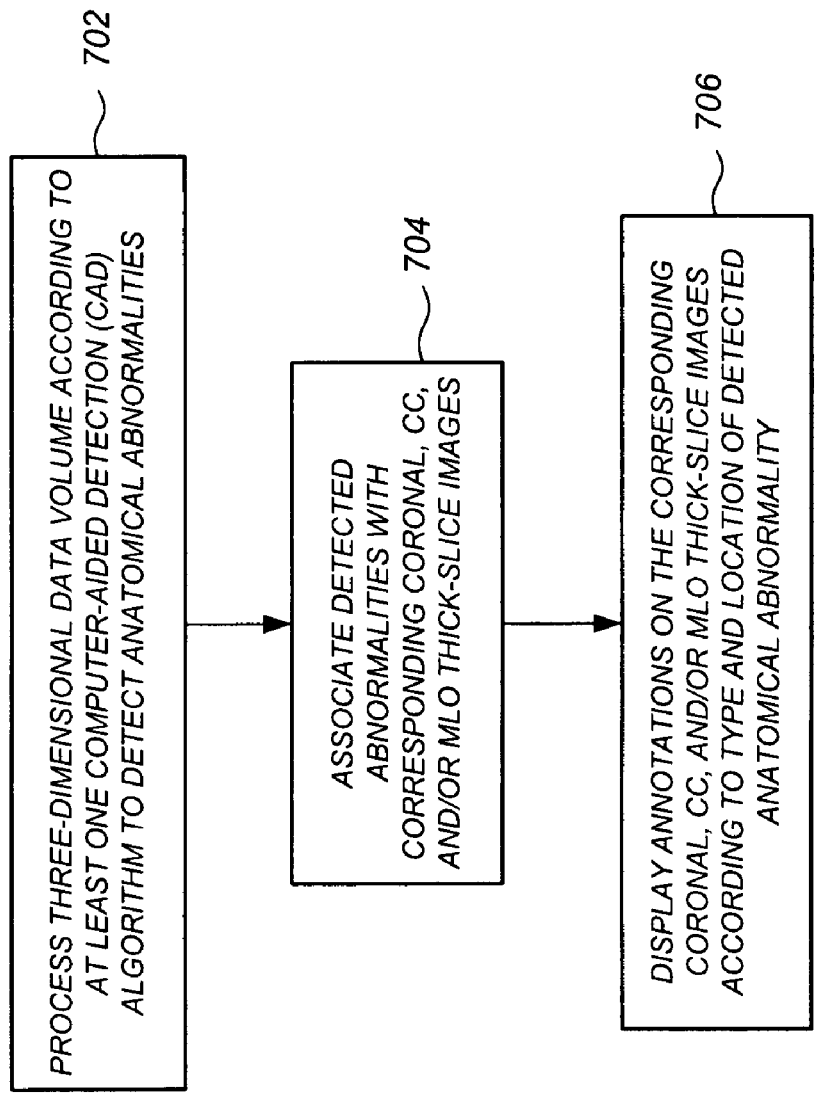
FIG. 7 illustrates a method for processing and displaying breast ultrasound information according to a preferred embodiment.

FIG. 7 illustrates a method for processing and displaying breast ultrasound information according to a preferred embodiment. At step 702, the three-dimensional data volume is processed according to at least one computer-aided detection (CAD) algorithm to detect anatomical abnormalities therein. These CAD algorithms can be the same as used supra for enhancing the visual appearance of lesions in the thick-slice images, or alternatively can be different and/or additional CAD algorithms. At step 704, the detected lesions in the three-dimensional data volume are mapped into their corresponding coronal thick-slice images. The detected lesions are also mapped into their corresponding CC and/or MLO thick-slice images if present. At step 706, annotations are superimposed on the corresponding coronal, CC, and/or MLO thick-slice images according to type and location of detected anatomical abnormality.

Figure 8:
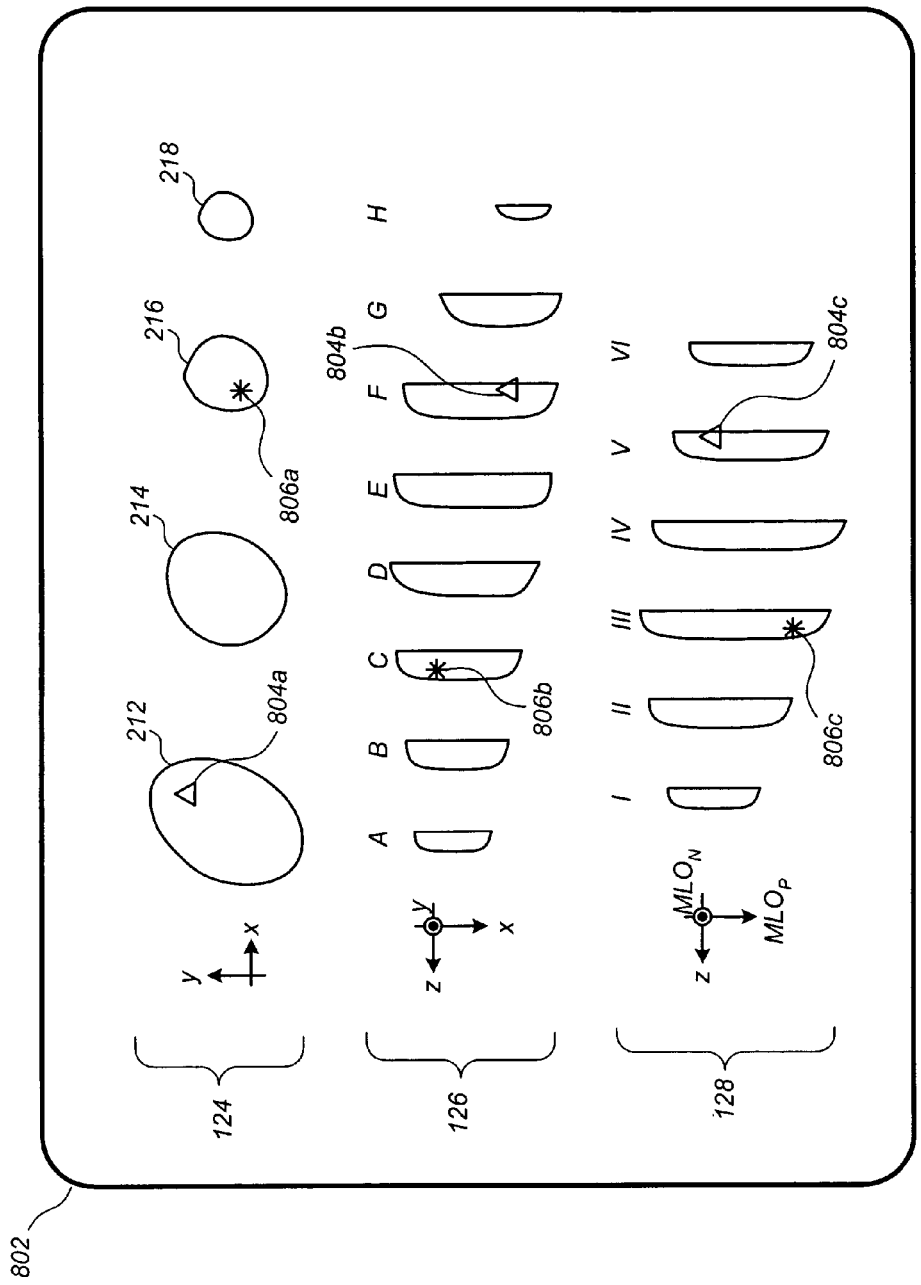
FIG. 8 illustrates a user display according to a preferred embodiment.

FIG. 8 illustrates a viewing workstation 802 according to a preferred embodiment, which is similar to the viewing workstation 122 but also includes CAD annotations on the coronal, CC, and MLO thick-slice images. The CAD annotations are placed according to type and location of detected anatomical abnormality. In the example of FIG. 8, a CAD-detected suspicious microcalcification cluster is denoted by triangles 804a, 804b, and 804c on the appropriate members of the coronal, CC, and MLO thick-slice image arrays, respectively. A CAD-detected suspicious mass is denoted by asterisk-shaped markers 806a, 806b, and 806c on the appropriate members of the coronal, CC, and MLO thick-slice image arrays, respectively.

Figure 9:
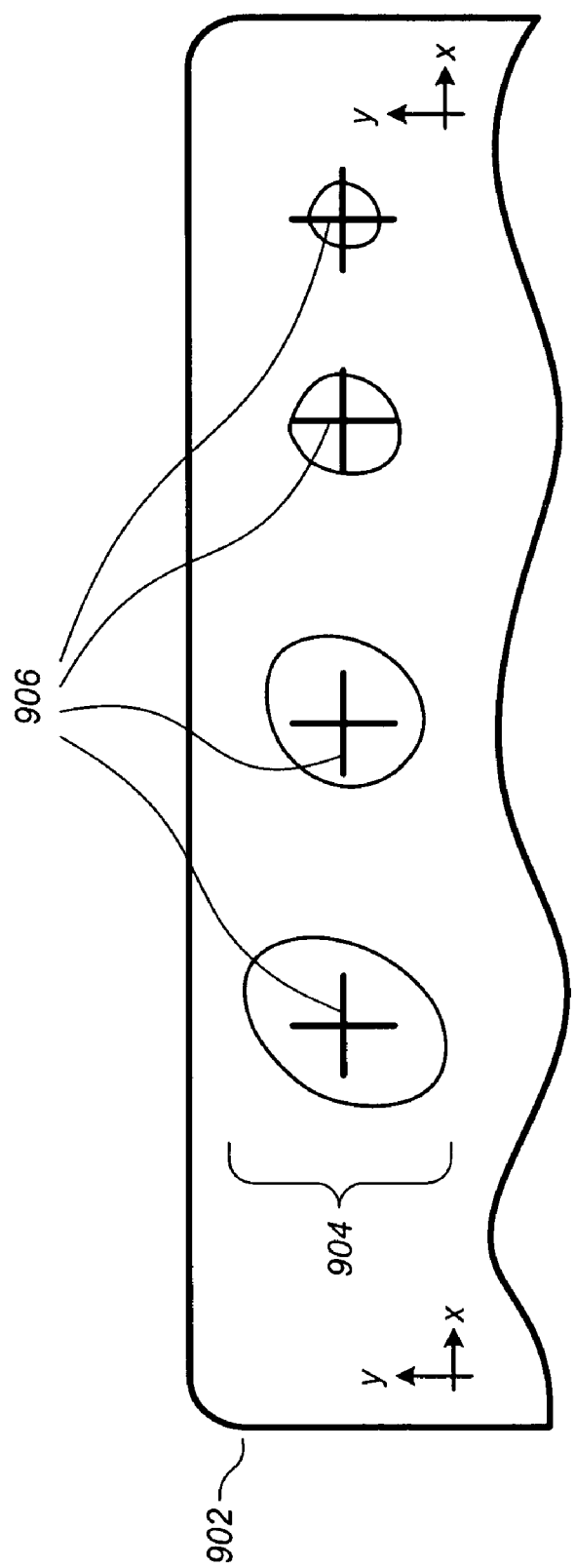
FIG. 9 illustrates a user display according to a preferred embodiment.

FIG. 9 illustrates a portion 902 of a viewing workstation according to a preferred embodiment, including an array 904 of coronal thick-slice images. It has been found useful to identify the x-y location of the nipple relative to the coronal thick-slice images on the user display, as indicated by the nipple markers 906. For example, it will not always be the case that the nipple will be at the center of each coronal thick-slice image, for anatomical reasons as well as the fact that there may be variations in the angle of attack of the chestward compressive force on the breast. These variations in the angle of attack may be unintentional, as in the case of imperfect patient positioning, or may be intentional, as in the case where a particular area of the breast (e.g., the upper inner quadrant) may be of concern in a follow-up scan. The position of the nipple can be determined using CAD algorithms on the three-dimensional data volume based on nipple shadow effects. Alternatively, the nipple position may be identified manually by the technician at the time of scanning, e.g., by ensuring that the nipple falls on a predetermined point on the compression plate, or by interacting with the scanning system based on a quick exploratory sweep across the breast by the probe, or by manually positioning the probe at the nipple location and pressing a nipple identification button, or by any of a variety of other manual nipple identification schemes.

Figure 10:
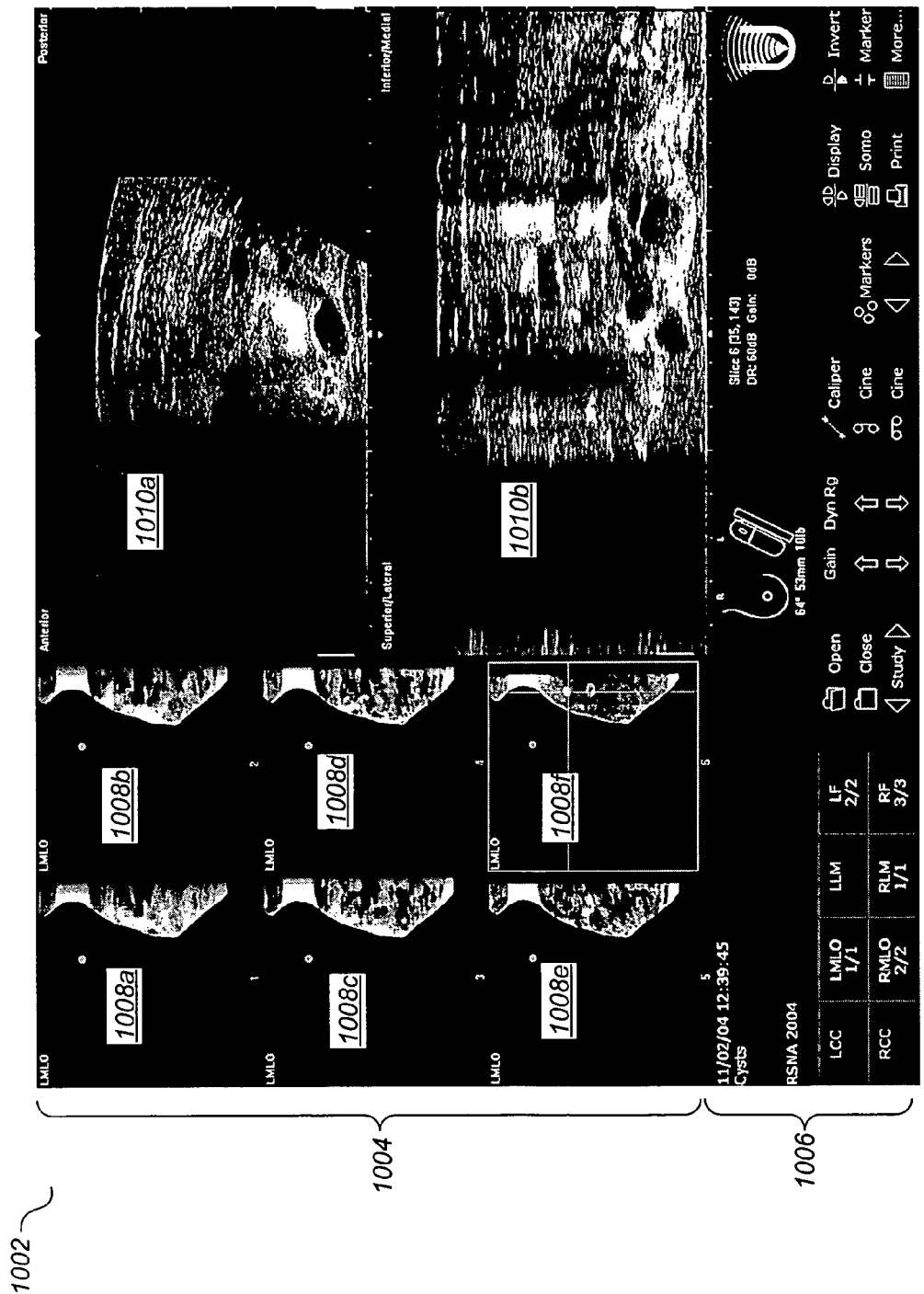
FIG. 10 illustrates a breast ultrasound display according to a preferred embodiment.

FIG. 10 illustrates a breast ultrasound display 1002 according to a preferred embodiment, generally comprising an image area 1004 and a menu bar 1006. In the particular display of FIG. 10, an array of six thick-slice images 1008a-1008e is displayed, as well as two planar ultrasound images 1010a-1010b. The display 1002 can be used in the viewing workstation 122 of FIG. 1, supra. The display 1002 can be used as part of a multi-modality PACS workstation, as a stand-alone device, and/or in conjunction with an x-ray mammography softcopy or hardcopy (i.e., lightbox) viewing station.

FIG. 11 illustrates a closer view of the menu bar 1006 comprising a variety of controls and information displays relating to the image area 1004. Menu bar 1006 comprises a body marker icon 1102, cine control (soft) buttons 1103, a marker display button 1104, marker navigation buttons 1106, a bilateral comparison control button 1108, a somogram button 1110, an invert button 1112, and a variety of file control buttons 1114. A designation of "/N" (N=2, 3, . . . ) on a view-related one of the file control buttons 1114 indicates that N sets of data are available for display for that view, e.g., N scans were taken corresponding to that view. The number preceding the "/N" denotes which of those sets is being displayed.

The cine control buttons 1103 allow the viewer to start a slice-by-slice ultrasound view cine loop sequence of the current breast view. It will start at the current cursor location, moving toward a first edge of the breast volume. It will delay there for a short period of time, then restart at the other edge of the breast volume. Pressing any button or moving the mouse while the cine is active will stop the cine loop, leaving the cursor at its most recent cine position. The invert button 1112 enables toggling of the thick-slice images between two different grayscale mapping modes, one for a generally white-on-black image mode, and another for a generally black-on-white image mode.

The bilateral comparison control button 1108 allows the viewer to dynamically toggle between displaying a bilateral comparison view format, as described further infra with respect to FIGS. 15-16 and FIGS. 19-20, or thick-slice views of a single breast. The somogram button 1110 allows the viewer to toggle between a first configuration in which only planar views are shown, a second configuration in which only thick-slice images are shown, and a third configuration in which combinations of thick-slice images and planar images are shown.

The marker display button 1104 allows the viewer to toggle between (i) non-annotated versions of the displayed images, and (ii) versions showing bookmarks as described further infra. The marker navigation buttons 1106 allow the viewer to perform bookmark-centric navigation wherein, upon selection, there is automatically displayed a corresponding one of the thick-slice images associated with a location of a next bookmark (forward) or prior bookmark (backward), as well as a one or more planar ultrasound images corresponding to that location. The bookmarks themselves may be entered by the viewer using a simple right-click and pull-down menu process, although the scope of the preferred embodiments is not so limited. By way of example, bookmarks may be provided by other users, automatically generated according to archived data, or by any of a variety of other processes.

Although not shown in FIG. 11, in another preferred embodiment there is provided a CAD display button and CAD navigation buttons providing similar navigational functionality as the marker display button 1104 and the marker navigation buttons 1106. In still another preferred embodiment, a nipple marker display button is provided for toggling between displaying nipple markers, described further infra, and not displaying nipple markers.

Body marker icon 1102 is automatically generated and provides fast communication of several different aspects of the images being displayed. A text section 1116 communicates a compression angle (for non-frontal, i.e., non-coronal, compression planes such as CC, MLO, LAT, etc.), a separation distance between compression plates (again for non-frontal compression planes), and a compression force used during the scans. The body marker icon 1102 further displays a compression plane 1117 against which the breast was compressed, a thick-slice depth marker 1118 corresponding to the depth of the displayed thick-slice image (when one thick-slice image is displayed), and a plane marker 1120 corresponding to a planar ultrasound image being displayed, if applicable.

FIG. 12 illustrates body marker icons for various non-frontal compression scenarios. The body marker icon 1202 corresponds to a LAT view of the right breast, the body marker icon 1204 corresponds to a CC view of the right breast, and the body marker icon 1206 corresponds to an MLO view of the left breast.

FIG. 13 illustrates body marker icons 1302, 1304, and 1306 for various frontal compression scenarios, each comprising a probe sweep indicator (e.g., 1303) indicating a trajectory and orientation of the linear scanning probe that scanned the breast. The body marker icon 1302 corresponds to a frontal scan of a medial side of the left breast in the inferior-to-superior direction, the body marker icon 1306 corresponds to a frontal scan of a medial side of the right breast in a direction close to the inferior-to-superior direction, and the body marker icon 1304 corresponds to a frontal scan of the center area of the left breast in a direction close to a lateral-to-medial direction.

Figure 14:
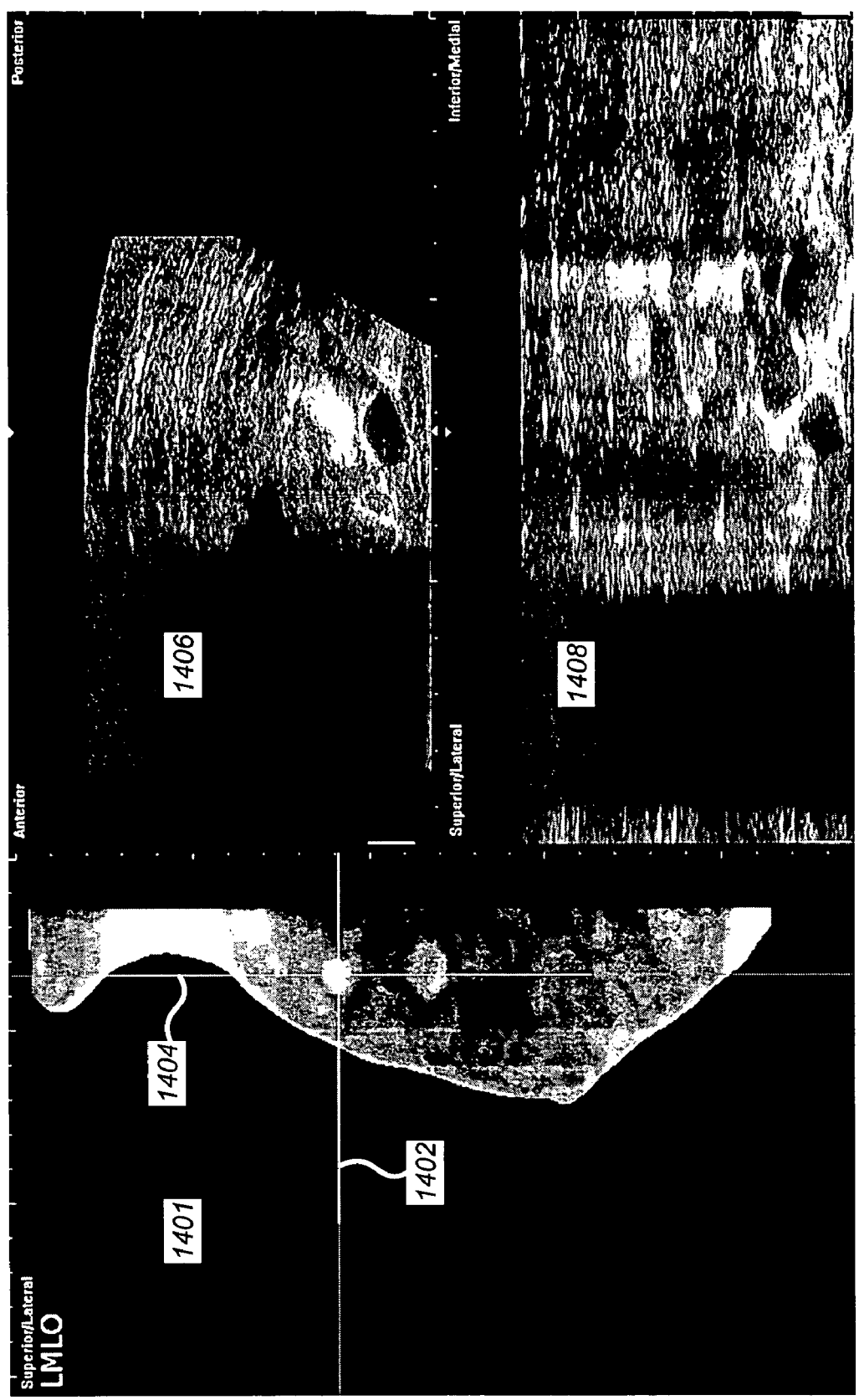
FIG. 14 illustrates a thick-slice image and planar views according to a preferred embodiment.

FIG. 14 illustrates a single thick-slice image 1401, which corresponds to the thick-slice image 1008*f* when the cursor is clicked at the location indicated in FIG. 10. It is to be appreciated that the menu bar 1006 is preferably displayed below all images but is omitted in this and subsequent figures for clarity. FIG. 14 further illustrates planar ultrasound images 1406 and 1408 corresponding respectively to the plane indicators 1402 and 1404, which intersect at the current cursor location.

Figure 15:
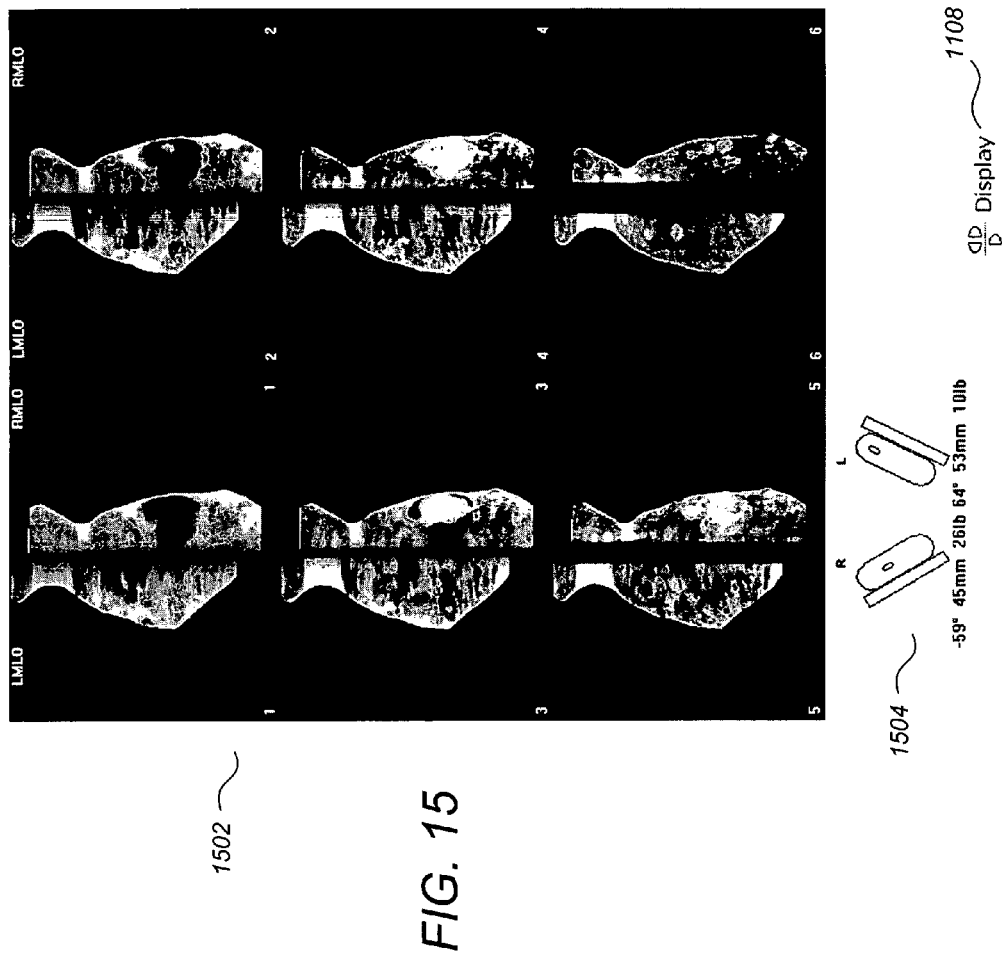
FIG. 15 illustrates a bilateral comparison array of thick-slice images, corresponding body marker icons, and a display control button according to a preferred embodiment.

FIG. 15 illustrates a bilateral comparison array 1502 of thick-slice images that is accessed by selection of the bilateral comparison control button 1108, comprising members of an LMLO thick-slice image array as positionally paired with corresponding members of an RMLO thick-slice image array, wherein the slab-like subvolumes of the left breast corresponding to the LMLO thick-slice image array have an at least general positionwise association with the slab-like subvolumes of the right breast corresponding to the RMLO thick-slice image array. A body marker icon 1504 illustrates the scanning orientations and other scanning parameters associated with each of the volumetric scans.

Figure 16:
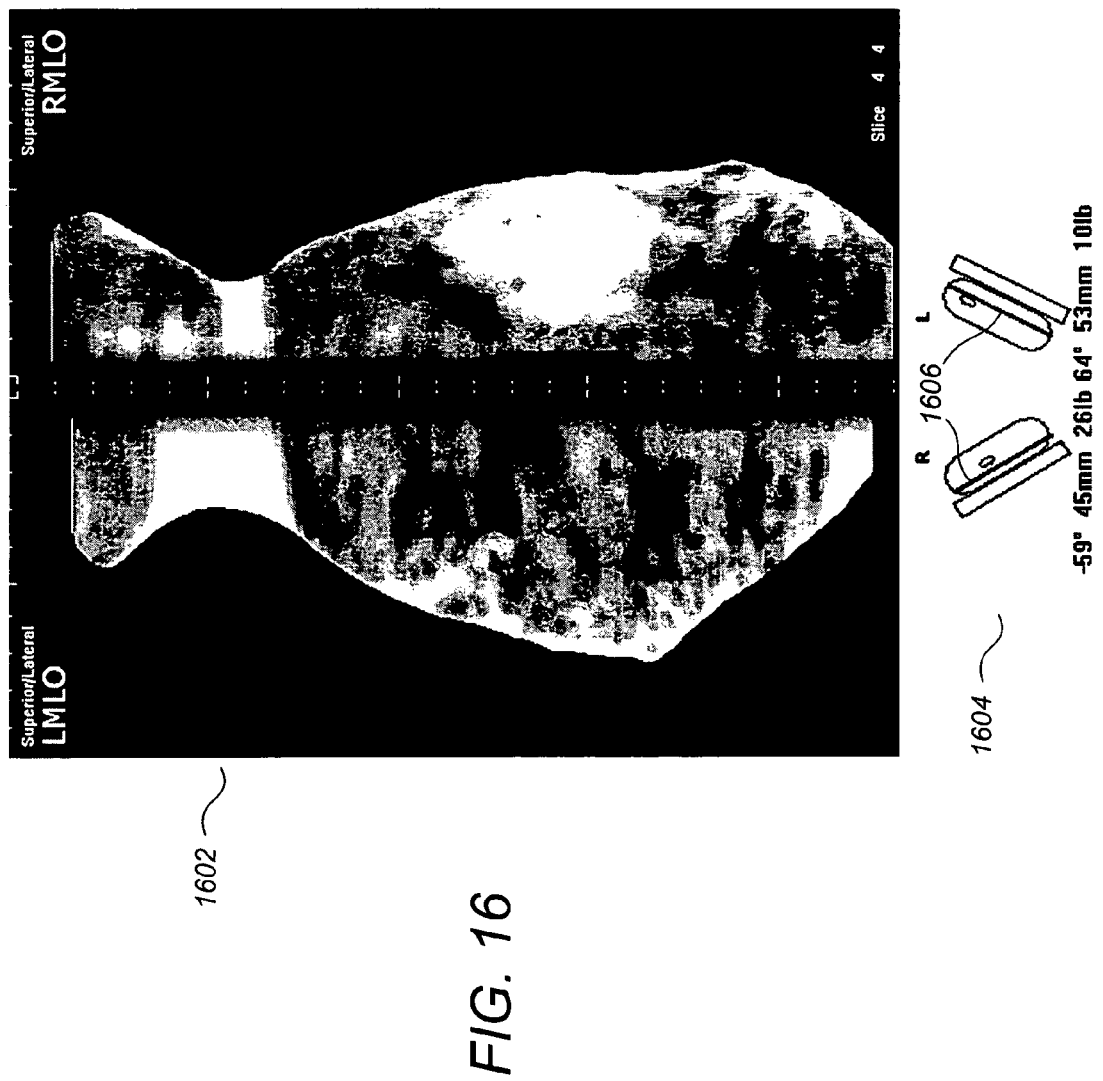
FIG. 16 illustrates a bilateral comparison view of thick-slice images and corresponding body marker icons according to a preferred embodiment.

FIG. 16 illustrates an expanded bilateral comparison view 1602 of the fourth thick-slice image pair of the bilateral comparison array 1502, which is displayed to when either of those fourth thick-slice images is clicked by the viewer on the display of FIG. 15. A body marker icon 1604 includes thick-slice depth markers 1606 showing the location of the fourth thick-slice subvolume within each of the left and right breasts. Nipple locations are also indicated on the body marker icon 1602.

Notably, it is not required that the associations between slab-like subvolumes of the left and right breasts be precise for the preferred embodiments of FIGS. 15-16. The opposing breasts can be of different sizes and there can be many incidental variations between the ways they were scanned. Nevertheless, it has been found highly useful to present thick-slice image data in bilateral comparison formats such as those of FIGS. 15-16. For example, breast symmetry is readily analyzed.

Figure 17:
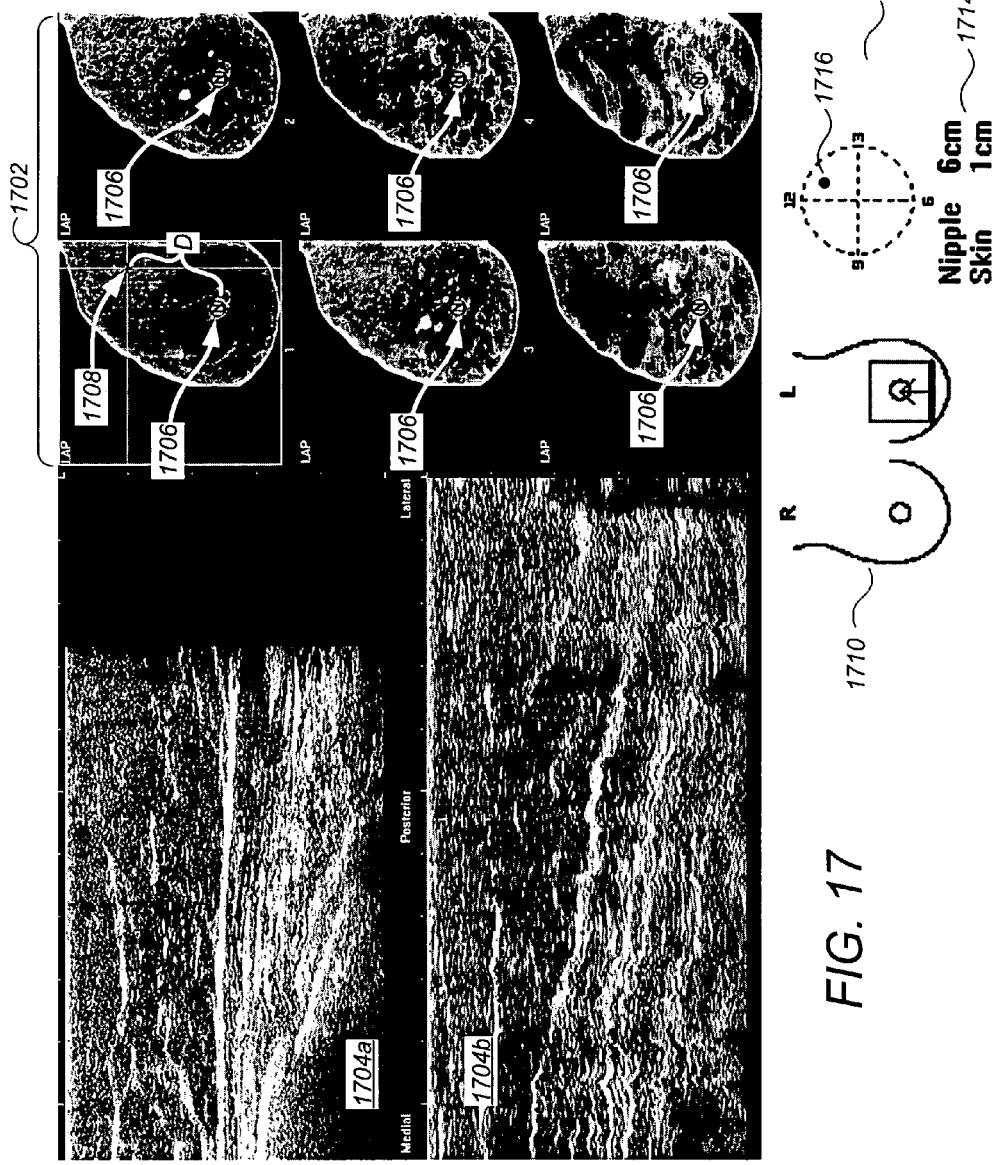
FIG. 17 illustrates an array of thick-slice images with nipple markers, a body marker icon, and a frontal breast icon according to a preferred embodiment.

FIG. 17 illustrates an array of thick-slice images 1702, two planar images 1704*a-b* corresponding to a current cursor position 1708 on a selected thick-slice image, a body marker icon 1710, nipple markers 1706, and a frontal breast icon 1712 according to a preferred embodiment. The nipple markers 1706 can be placed on the thick-slice images according to any of (i) a manually-entered nipple position provided with the associated volumetric ultrasound scan, (ii) a computer-derived nipple position automatically generated from the associated volumetric ultrasound scan, (iii) a computer-derived nipple position automatically generated based on manual placement of a physical nipple token for the associated volumetric ultrasound scan, and (iv) a viewer-determined position for the nipple marker. Physical nipple token can refer to a marker placed on the skin of the breast at the nipple location that is at least partially transparent to ultrasound but that also provides a degree of obscuration sufficient for automatic identification of its presence. Examples can include small silicone toroids, optionally with specks of metal therein, or any of a variety of other objects that can have similar effects. Physical nipple token can alternatively refer to a such a marker placed on the ultrasound scanning device itself, e.g., on one of the compression plates, at the nipple location.

Frontal breast icon 1712 comprises a cursor position indicator 1716 variably disposed thereon in a manner that reflects a relative position between the cursor 1708 and the nipple marker 1706 on the selected thick-slice image. Preferably, the frontal breast icon 1712 has a layout at least roughly resembling a clock face, and the cursor position indicator 1716 is positioned relative to the center of that clock face to reflect both (i) the distance "D" between the cursor 1708 and the nipple marker 1706, and (ii) the direction of the cursor 1708 from the nipple marker 1706 on the display (e.g., about 1:00 in the example of FIG. 17). The location of the cursor position indicator 1716 dynamically moves on the clock face as the cursor 1708 is moved around the thick-slice image. The combined display of the frontal breast icon 1712 and the body marker icon 1710 facilitates quick, intuitive comprehension of the physical and positional relevance of the images being displayed. Frontal breast icon 1712 further comprises a text portion 1714 numerically indicating (i) the distance "D," and (ii) the depth of the currently selected thick-slice image from the compressed surface across which the ultrasound probe was swept.

Figure 18:
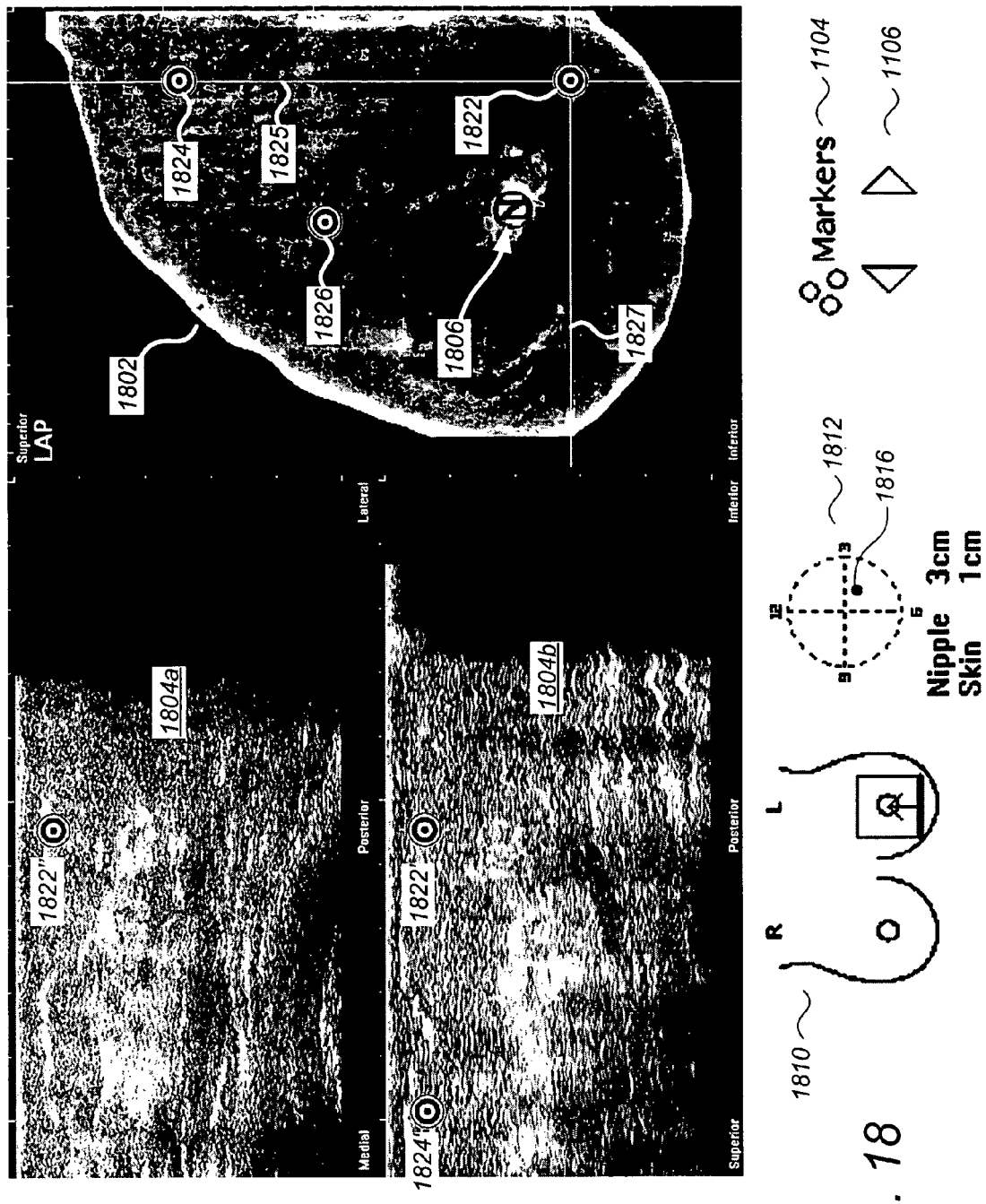
FIG. 18 illustrates a thick-slice image and planar images with displayed bookmarks, a body marker icon, a frontal breast icon, a marker display button, and marker navigation buttons according to a preferred embodiment.

FIG. 18 illustrates a thick-slice image 1802, two planar images 1804*a-b* corresponding to a current cursor position on the thick-slice image, a body marker icon 1810, nipple markers 1806, a plurality of bookmarks 1822, 1824, and 1826, and a frontal breast icon 1812. According to a preferred embodiment, the bookmarks are projected onto corresponding locations of the currently displayed planar images 1804*a-b*, if applicable, under an assumption that the bookmark spot is volumetrically in the middle plane of the slab-like subvolume corresponding to the thick-slice image. Accordingly, FIG. 18 illustrates corresponding bookmarks 1822' and 1824' on the superior-inferior planar image 1804*b*, because the bookmarks 1822 and 1824 lie along the vertical plane indicator 1825 passing through the current cursor location. The medial-lateral planar image 1804*a* only shows a corresponding bookmark 1822" because only the bookmark 1822 lies along the horizontal plane indicator 1827. Since neither plane indicator 1825 or 1827 intersects the bookmark 1826, there is no corresponding bookmark on the planar images 1804a-b for that bookmark.

The presence of all of the bookmarks can be toggled on and off by pressing the marker display button 1104. The marker navigation buttons 1106 allow the viewer to perform bookmark-centric navigation wherein, upon selection, the cursor is moved to a next bookmark (forward) or prior bookmark (backward), and the corresponding planar images are instantly displayed. As a default setting, navigation among the bookmarks is ordered in the same order as the bookmarks were entered by the viewer, although the scope of the preferred embodiments is not so limited. In the example of FIG. 18, the viewer has just pressed the one of the marker navigation buttons and has landed at the bookmark 1822. Notably, as indicated by the cursor position indicator 1816, the frontal breast icon 1812 keeps up automatically with the current cursor position, which in FIG. 18 is about 3 cm from the nipple marker location at a clock angle of roughly 4:00. The nipple markers and bookmarks can have any of a variety of shapes, sizes, colors, etc. without departing from the scope of the preferred embodiments.

FIG. 19 illustrates an array of thick-slice images 1902 with nipple markers 1906 that have been shifted by the viewer (using a click-and-drag method, for example). Although not necessarily warranted in this example (because the original position appears accurate based on nipple shadow positions), it may be desirable for the viewer to move the nipple marker location based on their observations, or on other extrinsic information. The position of the cursor 1908 relative to the nipple marker 1906 having shifted, the position of the cursor position indicator 1916 automatically shifts on the clock face of the frontal breast icon from 1916-old to 1916-new (e.g., from about 0.5 cm at 12:00 to about 3 cm at 4:00).

FIG. 20 illustrates an array of thick-slice images 2002 with bookmarks 2010, 2011, 2012, and 2013 placed thereon, for illustrating a multi-slice bookmark-centric navigation process according to a preferred embodiment. By the viewer clicking on the forward marker navigation button 1106, the cursor is instantly taken to the next bookmark, and corresponding planar images (not shown) are displayed.

Generally speaking, as in the example of FIG. 20, there will often be bookmarks on several of the thick-slice images. Convenient navigation analogous to that shown in FIG. 20 is provided when only one of the thick-slice images is displayed at a time (see, e.g., FIG. 14, supra). In particular, when only a single thick-slice image is being shown and one of the marker navigation buttons 1106 is pressed, the current thick-slice image is replaced (if applicable) with a next thick-slice image corresponding to a next bookmark, and the cursor is placed at the next bookmark in that thick-slice image with corresponding planar views being displayed. Rapid navigation among bookmarks is thereby achieved.

In another preferred embodiment, similar navigation capabilities are provided among CAD detections, i.e., by the viewer clicking on a CAD navigation button, the cursor is instantly taken to the next CAD marker location, and corresponding planar images are displayed. Among other advantages, bookmark-centric and/or CAD-centric navigation according to the preferred embodiments can substantially reduce the time needed to examine a case and increase radiologist productivity.

Figure 21:
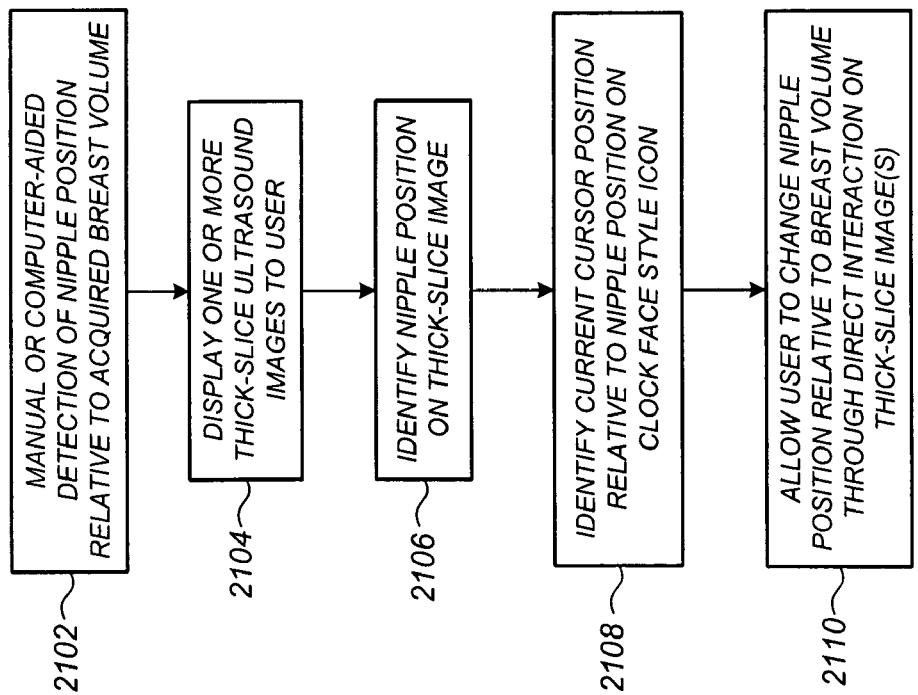

FIG. 21 illustrates breast ultrasound volume processing and display according a preferred embodiment. At step 2102, nipple position is obtained either manually or in an automated manner relative to an acquired breast volume that is preferably chestwardly-compressed for head-on scanning. At step 2104, one or more thick-slice ultrasound images is displayed. At step 2106, nipple markers are shown on the thick-slice image(s), the nipple marker positions representing a projection of the nipple location thereupon. At step 2108, the current cursor position relative to the displayed nipple marker position is communicated on a clock face style icon. At step 2110, the viewer is allowed to change the nipple marker position relative to the breast volume through direct interaction on thick-slice image(s).

Figure 22:
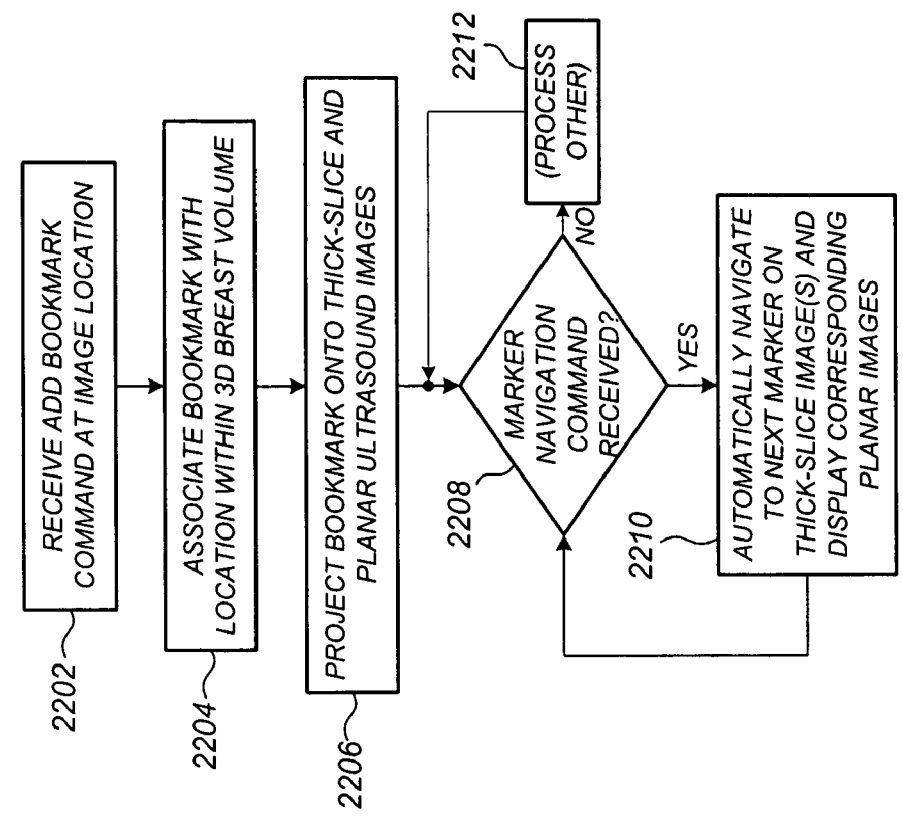
FIGS. 21 and 22 illustrate breast ultrasound volume acquisition, processing, and display according to one or more preferred embodiments.

FIG. 22 illustrates breast ultrasound volume processing and display according a preferred embodiment. At step 2202, bookmarks are added via bookmarking commands, e.g., through a right-click and drop-down menu style command upon a thick-slice image or a planar image. At step 2204, that bookmark location is associated with its corresponding location within the 3D breast volume. At step 2206, that bookmark is projected onto all relevant displayed thick-slice and planar ultrasound images as required to preoperly reflect its position in the 3D breast volume. If a marker navigation command is received at step 2208, then the display automatically navigates to a next bookmark location and shows the appropriate thick-slice image and corresponding planar images at step 2210.

Figure 23:
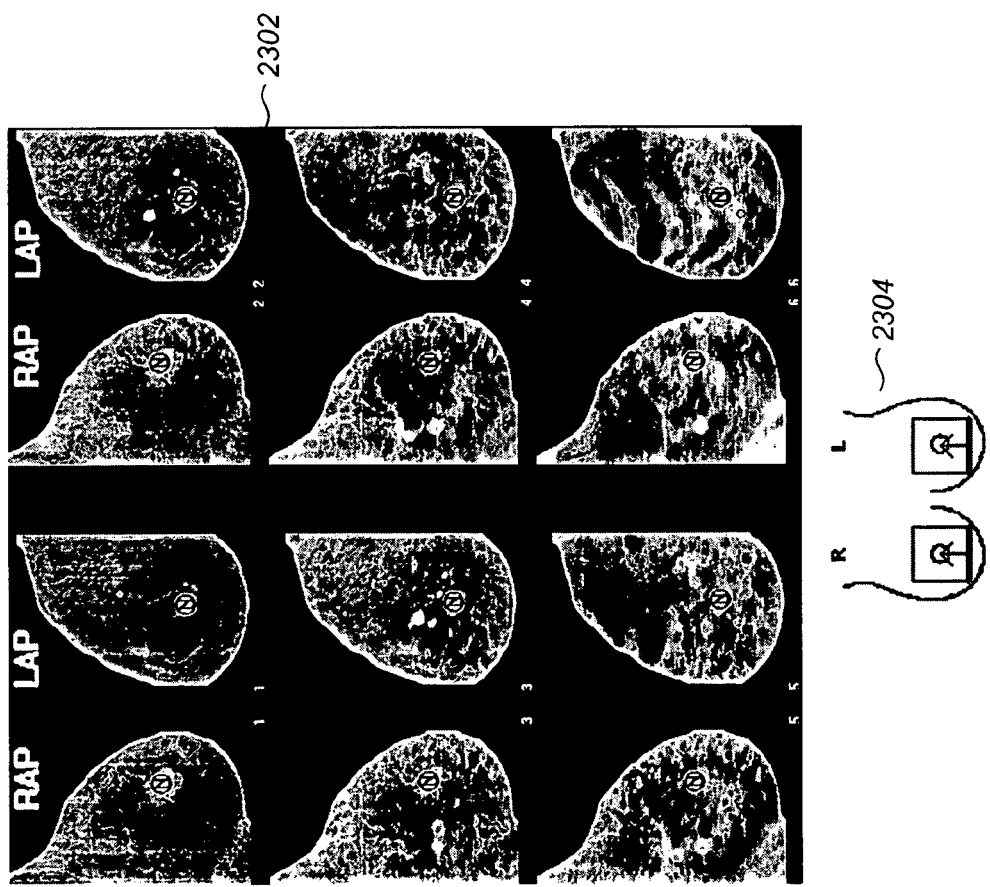
FIG. 23 illustrates a bilateral comparison array view of thick-slice images and corresponding body marker icons according to a preferred embodiment.

FIG. 23 illustrates a bilateral comparison array 2302 of thick-slice images that is easily navigated to by selection of the bilateral comparison control button 1108, supra, comprising members of an LAP (left anterior-posterior) thick-slice image array as positionally paired with corresponding members of an RAP (right anterior-posterior) thick-slice image array, wherein the slab-like subvolumes of the left breast corresponding to the LAP thick-slice image array have an at least general positionwise association with the slab-like subvolumes of the right breast corresponding to the RAP thick-slice image array. A body marker icon 2304 illustrates the scanning orientations for each breast volume.

Figure 24:
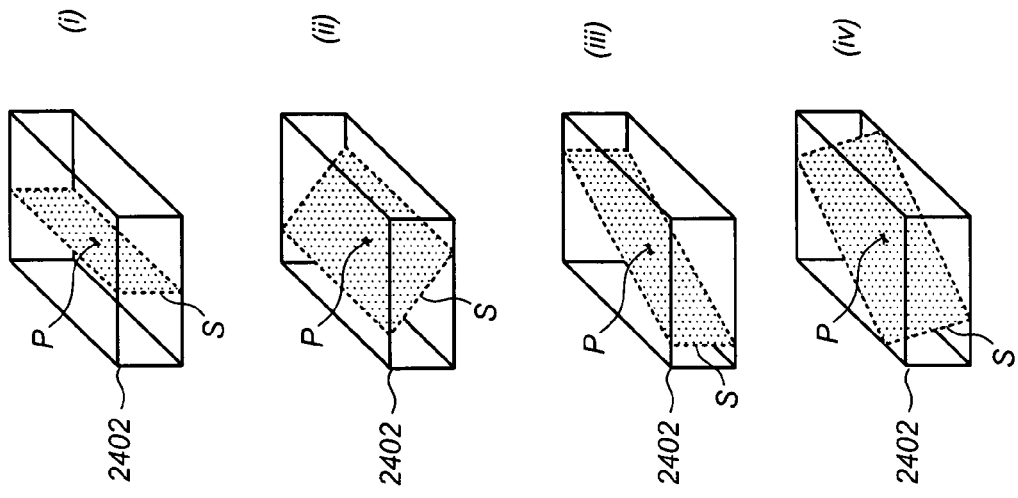
FIG. 24 illustrates examples of virtual probe reconstruction planes according to a preferred embodiment.

FIG. 24 illustrates examples of a virtual probe reconstruction (VPR) plane "S" around a point "P" within a breast volume 2402 according to a preferred embodiment. The viewer is provided with a pointing device, which can be the regular mouse in a particular mode, or which can be a separate joystick or similar control. With at least one thick-slice image and at least one planar image being displayed, the viewer can invoke a VPR command for the present cursor position. This causes the cursor to freeze at the present location "P" within the breast volume, wherein the viewer can then change the orientation of the plane "S" corresponding to the displayed planar image from a normal "vertical" position within the breast volume, see FIG. 24 at (i), to any of a variety of different orientations under control of the pointing device. For example, as indicated in FIG. 24, there is provided a roll capability, see FIG. 24 at (ii), a yaw capability, see FIG. 24 at (iii), and combinations of roll and yaw, see FIG. 24 at (iv).

FIG. 25 illustrates a full-breast composite thick-slice image 2502, corresponding planar images 2504a-b, a body marker icon 2510, and a frontal breast icon 2512 according to a preferred embodiment. Composite thick-slice image 2502 is preferably a CAD-enhanced expression of the sonographic properties of substantially the entire breast volume, i.e., all of the tissue imaged by the volumetric ultrasound scans. Any of a variety of CAD algorithms can be used such as those discussed U.S. Pat. No. 6,317,617, supra, and those described in the commonly assigned WO 03/101303 A1, supra. The lesions can then be enhanced according to their likelihood of malignancy (or other metric of interest) on the composite thick-slice image 2502. The composite thick-slice image 2502 can serve as a useful "guide" or "road map" for viewing the planar ultrasound images and the other thick-slice images, and can optionally be provided with explicit CAD markings near the enhanced lesion locations.

Figure 26:
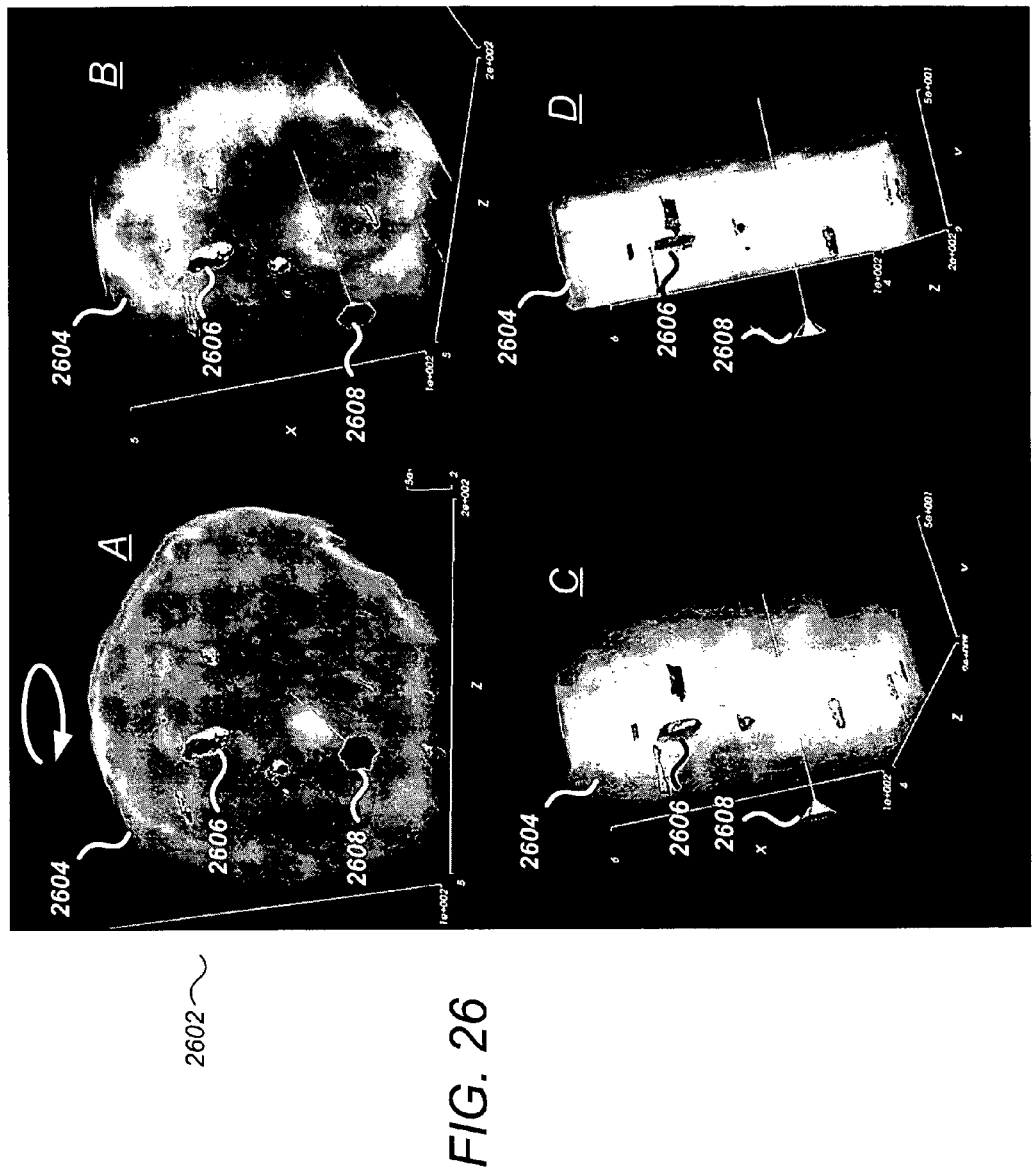
FIG. 26 illustrates a volume-rendered breast ultrasound volume with surface-rendered computer-assisted diagnosis (CAD) detections therein according to a preferred embodiment.

FIG. 26 illustrates a display 2602 comprising a volume-rendered breast ultrasound volume 2604 with surface-rendered computer-assisted diagnosis (CAD) detections 2606 therein according to a preferred embodiment. A three-dimensional nipple marker 2608 is provided to properly orient the viewer in visualizing the breast volume. In one preferred embodiment, the volume-rendered breast ultrasound volume 2604 is rotated in a cine-like fashion, as indicated by the sequence A-D in FIG. 26.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although primarily described supra in the context of ultrasound imaging, it is to be appreciated that data from other full-field breast imaging modalities (e.g., MRI, CT, PET) can be advantageously processed and displayed according to one or more of the described preferred embodiments. One or more of the displays described herein is similar to SOMOGRAM™ displays provided by U-Systems, Inc. of San Jose, Calif. By way of further example, although described supra as being volumetrically segregated, the coronal slab-like subvolumes from which the coronal thick-slice images are computed can be partially overlapping, which can be useful in dealing with lesions that would otherwise straddle the borders of the subvolumes. By way of even further example, although most nipple markers are described in the preferred embodiments supra in the context of coronal thick-slice images, in other preferred embodiments the nipple markers are shown on the MLO, CC, and other thick-slice image views.

By way of further example, it is to be appreciated that substantially parallel to a coronal plane is used herein to generally reflect the practical realities of situations such as head-on scanning of the breast, and that there may be some deviation from the plane of the chest wall. For example, for a particular patient having highly pendulous breasts it might be found most optimal to compress the breast at some small angle, such as 15 degrees, away from the plane of the chest wall. In this case, slab-like subvolumes that are taken parallel to the plane of compression would still be considered substantially parallel to the coronal plane.

By way of still further example, in alternative preferred embodiments the coronal slab-like subvolumes described supra can be replaced by thin-slice coronal images, i.e. thin-slice planar ultrasound images along planes substantially parallel to a coronal plane. This can be particularly useful in a follow-up diagnosis setting in which fine details are desired for viewing. By way of still further example, in another alternative preferred embodiment, the clinician is given the ability to interchangeably switch among, or pick-and-choose between, displaying the coronal slab-like subvolumes and the thin-slice coronal images. Therefore, reference to the details of the preferred embodiments are not intended to limit their scope, which is limited only by the scope of the claims set forth below.

What is claimed is:

1. A method for presenting breast ultrasound information, comprising:
  generating a first thick-slice image representing a sonographic property within a first slab subvolume of a chestwardly compressed first breast of a patient by (i) imaging the chestwardly compressed first breast with an ultrasound imaging apparatus to thereby derive a first plurality of thin-slice images and (ii) computer-processing said first plurality of thin-slice images to thereby generate said first thick-slice image;
  generating a second thick-slice image representing said sonographic property within a second slab subvolume of a chestwardly compressed second breast of the patient by (i) imaging the chestwardly compressed second breast to thereby derive a second plurality of thin-slice images and (ii) computer-processing said second plurality of thin-slice images to thereby generate said second thick-slice image, said first and second slab subvolumes occupying generally similar positions within the first and second breasts, respectively, said first and second slab subvolumes each being substantially parallel to a coronal plane of the patient; and
  displaying said first and second thick-slice image adjacent each other for comparison of the first and second breasts relative to said sonographic property.

2. The method of claim 1, said first thick-slice image being a member of a first thick-slice image array corresponding to successive slab subvolumes within the first breast, said second thick-slice image being a member of a second thick-slice image array corresponding to successive slab subvolumes within the second breast, each slab subvolume within the second breast having at least a general positionwise association with a corresponding slab subvolume within the first breast, further comprising displaying a plurality of members of said first thick-slice image array as positionally paired with corresponding members of said second thick-slice image array.

3. The method of claim 2, wherein said successive slab subvolumes for each of said first and second breasts collectively occupy substantially all of the breast volume for that breast.

4. The method of claim 2, said sonographic property being associated with first and second breast volumes corresponding to said first and second breasts, respectively, further comprising:
  receiving a plurality of bookmarks, each bookmark identifying a bookmark location within one of said first and second breast volumes;
  receiving a bookmark navigation command; and
  automatically displaying (i) a corresponding one of said thick-slice images associated with a next bookmark location, and (ii) a planar ultrasound image corresponding to said next bookmark location, said planar ultrasound image representing said sonographic property along a plane passing through said next bookmark location within its associated first or second breast volume.

5. The method of claim 2, said sonographic property being associated with first and second breast volumes corresponding to said first and second breasts, respectively, further comprising:
  receiving a plurality of computer-aided detection (CAD) results, each CAD result identifying a potentially suspicious location within one of said first and second breast volumes;
  receiving a CAD navigation command; and
  automatically displaying (i) a corresponding one of said thick-slice images associated with a next CAD result location, and (ii) a planar ultrasound image corresponding to said next CAD result location, said planar ultrasound image representing said sonographic property along a plane passing through said next CAD result location within its associated first or second breast volume.

6. The method of claim 1, further comprising displaying a nipple marker on each of said first and second thick-slice images representing a projection of an associated nipple location thereupon.

7. The method of claim 6, said sonographic property being acquired during volumetric ultrasound scans obtaining first and second breast volumes corresponding to said first and second breasts, respectively, wherein each nipple marker is positioned on its associated thick-slice image according to at least one of (i) a manually-entered nipple position provided with the associated volumetric ultrasound scan, (ii) a computer-derived nipple position automatically generated from the associated volumetric ultrasound scan, (iii) a computer-derived nipple position automatically generated based on manual placement of a physical nipple token for the associated volumetric ultrasound scan, and (iv) a viewer-determined position for the nipple marker.

8. The method of claim 6, said first thick-slice image being displayed to a viewer on a display monitor having an associated pointing device, further comprising:
displaying a cursor upon the first thick-slice image according to a viewer manipulation of said pointing device; and
displaying a breast icon near said first thick-slice image, said breast icon including a cursor position indicator variably disposed thereon in a manner that reflects a relative position between said cursor and said nipple marker on said first thick-slice image.

9. The method of claim 8, wherein said breast icon is configured to at least roughly resemble a clock face, said cursor position indicator being positioned relative to a center of the clock face in a manner that reflects said position of said cursor relative to said nipple marker.

10. The method of claim 1, said first thick-slice image being displayed to a viewer on a display monitor having an associated pointing device, further comprising:
displaying a cursor position upon the first thick-slice image according to a viewer manipulation of said pointing device, said cursor position being associated with a corresponding point within the first breast volume; and
displaying a planar ultrasound image corresponding to said cursor position, said planar ultrasound image representing said sonographic property along a plane passing through said corresponding point within the first breast volume.

11. The method of claim 10, further comprising modifying an orientation of said plane around said corresponding point according to subsequent viewer manipulations of an orienting device.

12. The method of claim 1, wherein said slab subvolumes within the first and second breasts occupy substantially all of the volume of the first and second breasts, respectively, and wherein said first and second thick-sliced images are enhanced according to at least one computer-aided detection (CAD) algorithm operating on said first and second breast volumes.

13. The method of claim 1 said sonographic property being measured throughout a first breast volume corresponding to said first breast, further comprising:
receiving computer-aided diagnosis (CAD) information associated with the first breast volume identifying potentially suspicious regions therein;
displaying a volume rendering of said first breast volume according to said sonographic property thereof; and
displaying a surface rendering of at least one of said potentially suspicious regions within said volume rendering.

14. A method for presenting breast ultrasound information, comprising;
generating a thick-slice image representing a sonographic property of a chestwardly compressed breast of a patient within a slab subvolume thereof by (i) imaging the chestwardly compressed breast with an ultrasound imaging apparatus to thereby derive a plurality of thin-slice images and (ii) computer-processing said plurality of thin-slice images to thereby generate said thick-slice image;
wherein said slab subvolume has a thickness between 2 mm and 20 mm, and
wherein said slab subvolume is substantially parallel to a coronal plane of the patient, further comprising:
generating a nipple marker on said thick-slice image representing a projection of a nipple location thereupon, said sonograghic property being associated with a scan of a breast volume;
wherein said nipple marker is positioned on the thick-slice image according to at least one of
(i) a manually-entered nipple position provided with the scan, (ii) a computer-derived nipple position automatically generated from the scan,
(ii) (iii) a computer-derived nipple position automatically generated based on manual placement of a physical nipple token for the scans, and
(iii) a viewer-determined position for the nipple marker; and
displaying said first thick-slice image and said nipple marker on a computerized display.

15. The method of claim 14, said thick-slice image being a member of a thick-slice image array corresponding to successive slab subvolumes within the breast substantially parallel to the coronal plane, further comprising simultaneously displaying a plurality of members of said thick-slice image array.

16. The method of claim 15, wherein said successive slab subvolumes collectively occupy substantially all of the breast volume.

17. The method of claim 15, each of said thick-slice images being displayed to a viewer on a display monitor having an associated pointing device, further comprising:
displaying a cursor upon a selected one of said thick-slice images according to a viewer manipulation of said pointing device; and
displaying a breast icon on said display monitor, said breast icon including a cursor position indicator variably disposed thereon in a manner that reflects a relative position between said cursor and said nipple marker on said selected thick-slice image.

18. The method of claim 17, wherein said breast icon is configured to at least roughly resemble a clock face, said cursor position indicator being positioned relative to a center of the clock face in a manner that reflects said position of said cursor relative to said nipple marker.

19. The method of claim 14, said thick-slice image being displayed to a viewer on a display monitor having an associated pointing device, further comprising:
displaying a cursor position upon the thick-slice image according to a viewer manipulation of said pointing device, said cursor position being associated with a corresponding point within the breast volume; and
displaying a planar ultrasound image corresponding to said cursor position, said planar ultrasound image representing said sonographic property along a plane passing through said corresponding point within the breast volume.

20. The method of claim 19, further comprising modifying an orientation of said plane around said corresponding point according to subsequent viewer manipulations of an orienting device.

21. The method of claim 14, wherein said slab subvolume occupies substantially all of the breast volume, and wherein said thick-slice image is enhanced according at least one computer-aided detection (CAD)) algorithm operating on said breast volume.

22. The method of claim 14, said sonographic property being measured throughout the breast volume, further comprising:
receiving computer-aided diagnosis (CAD) inlbrmation associated with the breast volume identifying potentially suspicious regions therein;
displaying a volume rendering of said breast volume according to said sonographic property thereof; and
displaying a surface rendering of at least one of said potentially suspicious regions within said volume rendering.

23. A method for presenting breast ultrasound information, comprising:
generating a thick-slice image representing a sonographic property of a chestwardly compressed breast of a patient within a slab subvolume thereof by (i) imaging the chestwardly compressed breast with an ultrasound imaging apparatus to thereby derive a plurality of thin-slice images each representing a thin slice of the breast and (ii) computer-processing said plurality of thin-slice images to thereby generate said thick-slice image, wherein said slab subvolume is substantially parallel to a coronal plane of the patient;
displaying said thick-slice image on a computerized display;
generating and displaying a nipple marker on said thick-slice image representing a projection of a nipple location thereupon;
generating and displaying a cursor upon the thick-slice image according to a viewer manipulation of a pointing device associated with said display monitor; and
generating and displaying a breast icon near said thick-slice image, said breast icon including a cursor position indicator variably disposed thereon in a manner that reflects a relative position between said cursor and said nipple marker on said thick-slice image.

24. The method of claim 23, wherein said breast icon is configured to at least roughly resemble a clock face, said cursor position indicator being positioned relative to a center of the clock face in a manner that reflects said position of said cursor relative to said nipple marker.

25. The method of claim 23, said sonographic property being associated with scans of a breast volume, wherein said nipple marker is positioned on said thick-slice image according to at least one of (i) a manually-entered nipple position provided with the scan, (ii) a computer-derived nipple position automatically generated from the scans, (iii) a computer-derived nipple positioul automatically generated based on manual placement of a physical nipple token for the scans, and (iv) a viewer-determined position for the nipple marker.

26. The method of claim 23, further comprising:
receiving a plurality of bookmarks, each bookmark identifying a bookmark location within said slab subvolume; and
receiving a bookmark navigation command and, responsive thereto:
(i) automatically changing the cursor position to a next bookmark location; and
(ii) automatically displaying a planar ultrasound image corresponding to said next bookmark location, said planar ultrasound image representing said sonographic property along a plane passing through said next bookmark location within the breast volume.

27. The method of claim 23, further comprising:
receiving a plurality of computer-aided detection (CAD) results, each CAD result identifying a potentially suspicious location within the slab subvolume; and
receiving a CAD navigation command and, responsive thereto:
(i) automatically changing the cursor position to a next CAD result location; and
(ii) automatically displaying a planar ultrasound image corresponding to said next CAD result location, said planar ultrasound image representing said sonographic property along a plane passing through said next CAD result location within the breast volume.

28. A method for presenting breast ultrasound information comprising:
compressing a patient's breast chestwardly;
acquiring a plurality of thin-slice ultrasound images representing a three-dimensional volume of the patient's chestwardly compressed breast by scanning the chestwardly compressed patient's breast in an automated scanning process in a scanning direction with an ultrasound transducer that is long in a direction transverse to the scanning direction, wherein:
said thin-slice images conform to respective planes that are generally along the compression direction, and
each of said thin-slice imaacs represents a thin slice of the patient's breast;
generating a plurality of two-dimensional coronal thick-slice images from the three-dimensional data volume, each coronal thick-slice image:
representing said sonographic property of the breast as chestwardly compressed within a slab subvolume thereof substantially parallel to a coronal plane of the patient, and
representing a thick-slice of the patient's breast that is thicker than a slice represented by one of said thin-slice images; and
displaying said coronal thick-slice images on a user display.

29. The method of claim 28, further comprising:
generating a plurality of two-dimensional standard-plane thick-slice images from the three-dimensional data volume, said standard-plane thick-slice images representing said sonographic property of the breast within slab subvolumes thereof substantially parallel to a standard x-ray mammogram view plane;
concurrently displaying said standard-plane thick-slice images and said coronal thick-slice images on the user display.

30. The method of claim 29, wherein said standard x-ray mammogram view plane is the craniocaudal (CC) or the mediolateral oblique (MLO) view plane.

31. The method of claim 30, further comprising:
receiving an x-ray mammogram image of the breast corresponding to said standard x-ray mammogram view plane; and
concurrently displaying said x-ray mammogram image on said user display with said concurrent display of said standard-plane thick-slice images and said coronal thick-slice images.

32. The method of claim 31, each slab subvolume being defined between first and second planes substantially parallel to said coronal plane, each slab subvolume having a thickness as measured between said first and second planes between about 2 mm and 20 mm.

33. The method of claim 32, said thickness being between about 4 mm and 10 mm.

34. The method of claim 33, wherein all of said slab subvolumes have the same thickness.

35. The method of claim 34, wherein an average thickness of a first subset of said slab subvolumes located closer to a chest wall is less than an average thickness of a second subset of said slab subvolumes located farther from the chest wall, for detection of smaller structures nearer to the chest wall.

36. The method of claim 28, further comprising:
processing said three-dimensional data volume according to at least one computer-aided detection (CAD) algorithm to detect anatomical abnormalities in the breast;
associating said detected abnormalities with corresponding coronal thick-slice images based upon their relative position within the three-dimensional data volume; and
displaying annotations on said corresponding coronal thick-slice images according to type and location of detected anatomical abnormality.

\* \* \* \* \*